United States Patent
Pettersson

(10) Patent No.: US 10,206,757 B2
(45) Date of Patent: Feb. 19, 2019

(54) METHOD AND SYSTEM FOR DENTAL PLANNING AND PRODUCTION

(75) Inventor: Andreas Pettersson, Gothenburg (SE)

(73) Assignee: Nobel Biocare Services AG, Kloten (CH)

( * ) Notice: Subject to any disclaimer, the term of this patent is extended or adjusted under 35 U.S.C. 154(b) by 1088 days.

(21) Appl. No.: 12/522,706

(22) PCT Filed: Jan. 17, 2007

(86) PCT No.: PCT/EP2007/050426
§ 371 (c)(1),
(2), (4) Date: Sep. 28, 2010

(87) PCT Pub. No.: WO2008/083857
PCT Pub. Date: Jul. 17, 2008

(65) Prior Publication Data
US 2011/0008751 A1    Jan. 13, 2011

(30) Foreign Application Priority Data
Jan. 10, 2007    (SE) ..................................... 0700043

(51) Int. Cl.
  *A61C 1/08* (2006.01)
  *A61C 5/77* (2017.01)
  *A61C 13/00* (2006.01)

(52) U.S. Cl.
  CPC ................ *A61C 1/084* (2013.01); *A61C 5/77* (2017.02); *A61C 13/0004* (2013.01)

(58) Field of Classification Search
  CPC ........... A61C 1/0046; A61C 5/08; A61C 5/10; A61C 7/002; A61C 9/004; A61C 13/0003;
  (Continued)

(56) References Cited

U.S. PATENT DOCUMENTS

| 4,315,740 A | 2/1982 | Mercer et al. |
| 4,470,815 A | 9/1984 | Hazar |
| (Continued) | | |

FOREIGN PATENT DOCUMENTS

| EP | 0689804 A1 | 1/1996 |
| EP | 1205159 | 5/2002 |
| EP | 1317910 A1 | 6/2003 |
| EP | 1364625 A1 | 11/2003 |
| (Continued) | | |

OTHER PUBLICATIONS

International Search Report for for Application No. PCT/EP2007/050426 (the PCT counterpart of the present application), dated Oct. 24, 2007 in 3 pages.

(Continued)

*Primary Examiner* — Matthew Nelson
(74) *Attorney, Agent, or Firm* — Knobbe, Martens, Olson & Bear LLP

(57) ABSTRACT

A method and system useful for planning a dental restorative procedure of a patient and for producing at least one dental restoration or product related thereto to be used in the dental restorative procedure are disclosed. Input data from different sources, e.g. 3D data from a CT scan of a patient with a dental impression tray including a previously prepared dental impression of the patient in the patient's mouth, is matched with data from a high resolution 3D scan of the same dental impression. The resulting data is for instance matched by fiducial markers arranged at the dental impression tray.

17 Claims, 12 Drawing Sheets

(58) Field of Classification Search
CPC ... A61C 13/0004; A61C 19/04; G06T 7/0012;
G06T 17/00; G06T 2207/10072; G06T
2207/10116; G06T 2207/10081; G06T
2207/30004; G06T 2210/41; G05B
19/4097; G05B 19/4099; G05B 19/41865
USPC ............... 433/24, 215, 218, 223, 226, 229;
382/128, 131, 154; 700/97, 98, 118;
264/17, 18
See application file for complete search history.

(56) References Cited

U.S. PATENT DOCUMENTS

| | | | |
|---|---|---|---|
| 4,663,720 A | 5/1987 | Duret et al. | |
| 4,832,601 A | 5/1989 | Linden | |
| 4,836,778 A | 6/1989 | Baumrind et al. | |
| 4,850,870 A | 7/1989 | Lazzara et al. | |
| 4,906,420 A | 3/1990 | Brajnovic et al. | |
| 4,998,881 A | 3/1991 | Lauks | |
| 5,015,183 A | 5/1991 | Fenick | |
| 5,030,096 A | 7/1991 | Hurson et al. | |
| 5,062,800 A | 11/1991 | Niznick | |
| 5,106,300 A | 4/1992 | Voitik | |
| 5,213,502 A | 5/1993 | Daftary | |
| 5,320,529 A | 6/1994 | Pompa | |
| 5,350,297 A | 9/1994 | Cohen | |
| 5,448,472 A | 9/1995 | Mushabac | |
| 5,482,463 A | 1/1996 | Wilson et al. | |
| 5,531,520 A | 7/1996 | Grimson et al. | |
| 5,538,426 A | 7/1996 | Harding et al. | |
| 5,577,912 A | 11/1996 | Prins | |
| 5,605,457 A | 2/1997 | Bailey et al. | |
| 5,605,458 A | 2/1997 | Bailey et al. | |
| 5,607,304 A | 3/1997 | Bailey et al. | |
| 5,613,852 A | 3/1997 | Bavitz | |
| 5,636,989 A | 6/1997 | Somborac et al. | |
| 5,651,675 A | 7/1997 | Singer | |
| 5,662,473 A | 9/1997 | Rassoli et al. | |
| 5,681,167 A | 10/1997 | Lazarof | |
| 5,718,579 A | 2/1998 | Kennedy | |
| 5,725,376 A | 3/1998 | Poirier | |
| 5,727,942 A | 3/1998 | Hartmann | |
| 5,743,916 A | 4/1998 | Greenberg et al. | |
| 5,768,134 A | 6/1998 | Swaelens et al. | |
| 5,788,494 A | 8/1998 | Phimmasone | |
| 5,823,776 A | 10/1998 | Duerr et al. | |
| 5,851,115 A | 12/1998 | Andersson et al. | |
| 5,857,853 A | 1/1999 | Van Nifterick | |
| 5,876,204 A | 3/1999 | Day et al. | |
| 5,938,686 A | 8/1999 | Benderev et al. | |
| 5,939,211 A | 8/1999 | Mörmann | |
| 5,967,305 A | 10/1999 | Blonder et al. | |
| 5,967,777 A | 10/1999 | Klein et al. | |
| 5,989,028 A | 11/1999 | Niznick | |
| 6,015,289 A | 1/2000 | Andreiko et al. | |
| 6,049,743 A | 4/2000 | Baba | |
| 6,068,482 A | 5/2000 | Snow | |
| 6,081,739 A | 6/2000 | Lemchen | |
| 6,099,311 A | 8/2000 | Wagner et al. | |
| 6,152,731 A | 11/2000 | Jordan et al. | |
| 6,159,008 A | 12/2000 | Kumar | |
| 6,174,166 B1 | 1/2001 | Jörneus | |
| 6,217,332 B1 | 4/2001 | Kumar | |
| 6,227,861 B1 | 5/2001 | Cartledge et al. | |
| 6,254,639 B1 | 7/2001 | Peckitt | |
| 6,280,194 B1 | 8/2001 | Björn et al. | |
| 6,287,117 B1 | 9/2001 | Niznick | |
| 6,287,119 B1 | 9/2001 | Van Nifterick et al. | |
| 6,305,939 B1 | 10/2001 | Dawood | |
| 6,312,260 B1 | 11/2001 | Kumar et al. | |
| 6,315,562 B1 | 11/2001 | Kumar | |
| 6,319,000 B1 | 11/2001 | Branemark | |
| 6,319,006 B1 | 11/2001 | Scherer et al. | |
| 6,322,359 B1 | 11/2001 | Jordan et al. | |
| 6,364,660 B1 | 4/2002 | Durbin et al. | |
| 6,375,465 B1 | 4/2002 | Engman et al. | |
| 6,382,975 B1 | 5/2002 | Poirier | |
| 6,488,502 B1 | 12/2002 | Weber | |
| 6,561,805 B2 | 5/2003 | Kumar | |
| 6,619,958 B2 | 9/2003 | Beaty et al. | |
| 6,626,911 B1 | 9/2003 | Engman et al. | |
| 6,627,327 B2 | 9/2003 | Reidt et al. | |
| 6,640,150 B1 | 10/2003 | Perrson | |
| 6,660,400 B1 | 12/2003 | Hintersehr | |
| 6,671,539 B2* | 12/2003 | Gateno et al. | 600/426 |
| 6,672,870 B2 | 1/2004 | Knapp | |
| 6,692,254 B1 | 2/2004 | Kligerman et al. | |
| 6,705,863 B2 | 3/2004 | Phan et al. | |
| 6,726,478 B1 | 4/2004 | Isiderio et al. | |
| 6,788,986 B1 | 9/2004 | Traber et al. | |
| 6,793,491 B2 | 9/2004 | Klein et al. | |
| 6,814,575 B2 | 11/2004 | Poirier et al. | |
| 6,824,384 B1 | 11/2004 | Bompard et al. | |
| 6,827,575 B1 | 12/2004 | Jörneus | |
| 6,857,574 B2 | 2/2005 | Kim | |
| 6,879,712 B2 | 4/2005 | Tuncay et al. | |
| 6,979,196 B2 | 12/2005 | Nikolskiy et al. | |
| 6,997,707 B2 | 2/2006 | Germanier | |
| 7,021,934 B2 | 4/2006 | Aravena | |
| 7,027,642 B2 | 4/2006 | Rubbert et al. | |
| 7,133,042 B2 | 11/2006 | Ahn et al. | |
| 7,175,435 B2 | 2/2007 | Andersson et al. | |
| 7,234,937 B2 | 6/2007 | Sachdeva et al. | |
| 7,245,753 B2 | 7/2007 | Squilla | |
| 7,322,824 B2 | 1/2008 | Schmitt | |
| 7,331,786 B2 | 2/2008 | Poirier | |
| 7,338,286 B2 | 3/2008 | Porter et al. | |
| 7,347,690 B2 | 3/2008 | Jordan et al. | |
| 7,373,286 B2 | 5/2008 | Nikolskiy et al. | |
| 7,551,760 B2 | 6/2009 | Scharlack et al. | |
| 7,572,125 B2 | 8/2009 | Brajnovic | |
| 7,702,492 B2 | 4/2010 | Marshall | |
| 7,717,708 B2 | 5/2010 | Sachdeva et al. | |
| 7,736,147 B2 | 6/2010 | Kaza et al. | |
| 7,762,814 B2* | 7/2010 | van der Zel | 433/201.1 |
| 7,835,811 B2 | 11/2010 | Schmitt | |
| 7,840,042 B2 | 11/2010 | Kriveshko et al. | |
| 7,845,943 B2 | 12/2010 | Meitner | |
| 7,865,261 B2 | 1/2011 | Pfeiffer | |
| 7,916,911 B2 | 3/2011 | Kaza et al. | |
| 7,942,668 B2 | 5/2011 | Brajnovic et al. | |
| 7,950,924 B2 | 5/2011 | Brajnovic | |
| 8,142,192 B2 | 3/2012 | Malo | |
| 8,157,565 B2 | 4/2012 | Jones et al. | |
| 8,170,327 B2 | 5/2012 | Glor et al. | |
| 8,186,999 B2 | 5/2012 | Andersson et al. | |
| 8,234,000 B2 | 7/2012 | Andersson et al. | |
| 8,805,658 B2 | 8/2014 | Pettersson et al. | |
| 9,937,023 B2 | 4/2018 | Andersson et al. | |
| 2002/0028417 A1 | 3/2002 | Chapoulaud et al. | |
| 2002/0064759 A1 | 5/2002 | Durbin et al. | |
| 2002/0102517 A1 | 8/2002 | Poirier | |
| 2002/0106604 A1 | 8/2002 | Phan et al. | |
| 2002/0125592 A1 | 9/2002 | Schulman et al. | |
| 2002/0177104 A1 | 11/2002 | Klein et al. | |
| 2003/0186187 A1 | 10/2003 | Germanier | |
| 2004/0015327 A1* | 1/2004 | Sachdeva | A61C 7/00 702/167 |
| 2004/0146830 A1* | 7/2004 | Weinstein | 433/76 |
| 2004/0184643 A1* | 9/2004 | Stantchev et al. | 382/128 |
| 2004/0204787 A1 | 10/2004 | Kopelman et al. | |
| 2004/0219490 A1 | 11/2004 | Gartner et al. | |
| 2004/0259051 A1 | 12/2004 | Brajnovic et al. | |
| 2005/0089822 A1 | 4/2005 | Geng | |
| 2005/0117693 A1* | 6/2005 | Miyano | A61B 6/0478 378/4 |
| 2005/0170311 A1 | 8/2005 | Tardieu et al. | |
| 2005/0177261 A1 | 8/2005 | Durbin et al. | |
| 2006/0008763 A1 | 1/2006 | Brajnovic et al. | |
| 2006/0008770 A1 | 1/2006 | Brajnovic et al. | |
| 2006/0040236 A1 | 2/2006 | Schmitt | |
| 2006/0106484 A1 | 5/2006 | Saliger et al. | |
| 2006/0155184 A1* | 7/2006 | Florent | G06T 7/0012 600/407 |

(56) References Cited

U.S. PATENT DOCUMENTS

| | | | |
|---|---|---|---|
| 2006/0240378 | A1 | 10/2006 | Weinstein et al. |
| 2006/0275736 | A1 | 12/2006 | Wen et al. |
| 2007/0190481 | A1 | 8/2007 | Schmitt |
| 2007/0281270 | A1 | 12/2007 | Brajnovic |
| 2008/0026338 | A1* | 1/2008 | Cinader .......... A61C 1/084 433/29 |
| 2008/0038692 | A1 | 2/2008 | Andersson et al. |
| 2008/0057466 | A1 | 3/2008 | Jordan et al. |
| 2008/0118895 | A1 | 5/2008 | Brajnovic |
| 2008/0153065 | A1 | 6/2008 | Brajnovic et al. |
| 2008/0220390 | A1 | 9/2008 | Klien |
| 2009/0113714 | A1 | 5/2009 | Greenberg |
| 2009/0187393 | A1 | 7/2009 | Van Lierde et al. |
| 2009/0220134 | A1 | 9/2009 | Cahill et al. |
| 2009/0220916 | A1 | 9/2009 | Fisker et al. |
| 2009/0304302 | A1 | 12/2009 | Kordass et al. |
| 2009/0316966 | A1 | 12/2009 | Marshall et al. |
| 2009/0325122 | A1 | 12/2009 | Brajnovic et al. |
| 2010/0105009 | A1 | 4/2010 | Karkar et al. |
| 2010/0124731 | A1 | 5/2010 | Groscurth et al. |
| 2010/0191510 | A1 | 7/2010 | Kopelman |
| 2010/0240001 | A1 | 9/2010 | Steger |
| 2010/0324875 | A1 | 12/2010 | Kalili |
| 2010/0332248 | A1 | 12/2010 | Pettersson |
| 2011/0008751 | A1 | 1/2011 | Pettersson |
| 2011/0010187 | A1 | 1/2011 | Andersson et al. |
| 2011/0013827 | A1 | 1/2011 | Orth et al. |
| 2011/0045431 | A1 | 2/2011 | Groscurth et al. |
| 2012/0123576 | A1 | 5/2012 | Pettersson |
| 2012/0290116 | A1 | 11/2012 | Andersson et al. |

FOREIGN PATENT DOCUMENTS

| | | | |
|---|---|---|---|
| EP | 1 486 900 | | 12/2004 |
| EP | 1500380 | | 1/2005 |
| EP | 1 982 650 | | 10/2008 |
| EP | 2 229 914 | | 9/2010 |
| EP | 2 327 372 | | 6/2011 |
| FR | 2836372 | A1 | 8/2003 |
| GB | 1131948 | | 10/1968 |
| JP | 2004 521671 | | 7/2004 |
| JP | 2005-532838 | | 11/2005 |
| JP | 2006-191985 | A | 7/2006 |
| WO | WO 94/14388 | A1 | 7/1994 |
| WO | WO 96/37163 | A1 | 11/1996 |
| WO | WO 97/49351 | | 12/1997 |
| WO | WO 98/16163 | | 4/1998 |
| WO | WO 98/44865 | A1 | 10/1998 |
| WO | WO 99/26540 | | 6/1999 |
| WO | WO 00/27300 | | 5/2000 |
| WO | WO 00/28914 | | 5/2000 |
| WO | WO 2001/050977 | | 7/2001 |
| WO | WO 01/54609 | | 8/2001 |
| WO | WO 01/58379 | A1 | 8/2001 |
| WO | WO 02/38074 | | 5/2002 |
| WO | WO 02/053055 | A1 | 7/2002 |
| WO | WO 02/053056 | A1 | 7/2002 |
| WO | WO 02/053057 | A1 | 7/2002 |
| WO | WO 2002/053056 | | 7/2002 |
| WO | WO 03/060825 | A2 | 7/2003 |
| WO | WO 04/098378 | A3 | 11/2004 |
| WO | WO 2005/055856 | | 6/2005 |
| WO | WO 06/082198 | | 1/2006 |
| WO | WO 2006/013074 | | 2/2006 |
| WO | WO 2006/014131 | | 2/2006 |
| WO | WO 2006031096 | A1 * | 3/2006 ............ A61C 13/00 |
| WO | WO 2007/009719 | | 1/2007 |
| WO | WO 07/129955 | | 11/2007 |

OTHER PUBLICATIONS

International Preliminary Report on Patentability and Written Opinion for Application No. PCT/SE 2001/002898 (the counterpart of U.S. Appl. No. 10/451,535 completed on Dec. 9, 2002 in 5 pages.

International Preliminary Report on Patentability and Written Opinion for Application No. PCT/SE 2007/000431 (the counterpart of U.S. Appl. No. 12/299,598) dated Apr. 9, 2007 in 13 pages.

International Search Report for Application No. PCT/SE 2001/002898 (the counterpart of the U.S. Appl. No. 10/451,535 dated Nov. 4, 2002 in 4 pages.

Tardieu, Philippe B. : "Aide Informatique Aux Diagnostics Et Aux Traitement Implantaires. Guides Chirurgico-Scannographiques. Programme Simm:Plan." Believed to be published in 1999. pp. 1-27.

European Patent Office Communication Pursuant to Rule 114(2) EPC with Third Party Observation Letter dated Mar. 6, 2009 in 4 pages, received in corresponding EP Application No. 02793696.2 (EP counterpart of 290C1).

Gateno et al., A New Technique for the Creation of a Computerized Composite Skull Model, J Oral Maxillofac Surg, 2003, vol. 61, pp. 222-227.

International Preliminary Report on Patentability and Written Opinion for Application No. PCT/SE 2003/001975 (the PCT counterpart of U.S. Appl. No. 11/172,291) dated Feb. 2, 2005 in 4 pages.

International Preliminary Report on Patentability and Written Opinion for Application No. PCT/SE 2004/001527 (the PCT counterpart of co-pending U.S. Appl. No. 10/582,417) dated Jan. 21, 2005 in 7 pages.

International Preliminary Report on Patentability and Written Opinion for Application No. PCT/SE 2005/001074 (the PCT counterpart of co-pending U.S. Appl. No. 11/573,193 dated Nov. 2, 2005 in 7 pages.

International Preliminary Report on Patentability and Written Opinion for Application No. PCT/SE 2005/001075 (the counterpart of the co-pending U.S. Appl. No. 11/573,196) dated Nov. 2, 2005 in 7 pages.

International Preliminary Report on Patentability for Application No. PCT/SE 2002/02393 (the PCT counterpart of co-pending U.S. Appl. No. 10/710,170) completed on Mar. 8, 2004 in 3 pages.

International Search Report for Application No. PCT/SE 2002/02393 (the PCT counterpart of co-pending U.S. Appl. No. 10/710,170) dated Mar. 20, 2003 in 2 pages.

International Search Report for Application No. PCT/SE 2003/001975 (the PCT counterpart of U.S. Appl. No. 11/172,291) completed on Feb. 2, 2005 in 4 pages.

International Search Report for Application No. PCT/SE 2003/001976 (the PCT counterpart of abandoned U.S. Appl. No. 11/172,354 and co-pending U.S. Appl. No. 12/014,031) dated Mar. 11, 2004 in 2 pages.

International Search Report for Application No. PCT/SE 2004/001527 (the PCT counterpart of co-pending U.S. Appl. No. 10/582,417) dated Jan. 21, 2005 in 3 pages.

International Search Report for Application No. PCT/SE 2005/001074 (the PCT counterpart of co-pending U.S. Appl. No. 11/573,193 dated Nov. 2, 2005 in 3 pages.

International Search Report for Application No. PCT/SE 2005/001075 (the counterpart of the co-pending U.S. Appl. No. 11/573,196).

International Search Report for Application No. PCT/SE 2007/000431 (the counterpart of U.S. Appl. No. 12/299,598) dated Apr. 9, 2007 in 4 pages.

Tardieu P.: 'Computer assistance in the planning and implementation of implant treatments. The Materialise concept and the SurgiCase Programme.' www.dentalespace.com 2000, pp. 1-11.

Tardieu P.B. and B. Philippe: 'Total maxillary edentation with terminal osseus atrophy therapeutic treatment' IMPLANT vol. 7, No. 3, 2000, pp. 199-210.

"Dental radiography," http://en.wikipedia.org/wiki/Dental_radiography, last modified on Jul. 4, 2013, Retrieved on Nov. 21, 2013, in 5 pages.

Ganz, "Presurgical Planning With CT-Derived Fabrication of Surgical Guides," American Association of Oral Maxillofacial Surgeons, 2005, 59-71.

Balshi et al., "Surgical Planning and Prosthesis Construction Using Computed Tomography, CAD/CAM Technology, and the Internet for Immediate Loading of Dental Implants," Journal Compilation, 18, 2006, 312-323.

(56) References Cited

OTHER PUBLICATIONS

U.S. Appl. No. 12/447,467, (U.S. Pat. No. 8,234,000), Method and Apparatus for Obtaining Date for a Dental Component and a Physical Dental Model, filed Jun. 24, 2009.
U.S. Appl. No. 13/562,132 (U.S. Pat. No. 9,937,023), Method and Apparatus for Obtaining Data for a Dental Component and a Physical Dental Model, filed Jul. 30, 2012.
U.S. Appl. No. 12/933,140 (U.S. Pat. No. 8,805,658), Repositioning of Components Related to Cranial Surgical Procedures in a Patient, filed Nov. 23, 2010.

\* cited by examiner

METHOD AND SYSTEM FOR DENTAL PLANNING AND PRODUCTION

CROSS-REFERENCE TO RELATED APPLICATIONS

This application is a national stage application under 35 U.S.C. § 371 of PCT Application No. PCT/EP2007/050426 designating the United States, filed on Jan. 17, 2007. The PCT Application was published in English, as WO 2008/083857 A1 on Jul. 17, 2008, and claims the benefit of the earlier filing date of Swedish Patent Application No. 0700043-3, filed Jan. 10, 2007. The contents of PCT Application No. PCT/EP2007/050426, including publication WO 2008/083857 A1, and Swedish Patent Application No. 0700043-3, are incorporated herein by reference in their entirety.

BACKGROUND

Field of the Invention

This disclosure pertains in general to the field of dentistry. More particularly the disclosure relates to a method and system for planning of dental restorative procedures and for producing dental restorations and/or products related to the dental restorative procedures.

Description of the Related Art

In dental repair applications, conventionally a working dental cast in plaster of the patient's dentition was often provided, which was made by means of impressions taken from the patient and filled with plaster. The working dental cast was then mounted in an articulator with the aid of a bite index taken, ensuring the correct positioning and registering of the dental cast. The dental restoration was then produced on the working dental cast obtained. Accuracy was checked by means of the articulator.

However, this type of production comprised a multitude of time consuming manual working operations that had to be performed. A rationalizing step was to scan the working cast with a three-dimensional (3-D) scanner, e.g. Procera Forte®. Subsequently, the dental restoration was electronically designed, e.g. by means of the Procera® CAD system. From the CAD data obtained, the dental restoration, such as a bridge, was manufactured. Veneering was eventually performed and the dental restoration was Procera® CAD system. From the CAD data obtained, the dental restoration, such as a bridge, was manufactured. Veneering was eventually performed and the dental restoration was finalized by grinding, and checking with help of the articulator. Finally, the dental restoration was installed in the patient. Still, a plaster cast was necessary, and manual working operations related thereto were required, including grinding of the plaster cast, drilling of holes in the plaster cast, pinning of the plaster cast, casting of a supporting base plate, grinding of the base plate, sectionizing of the plaster cast, etc.

Improved systems have been presented in the international applications WO02/053056 and WO2005/055856 of the same applicant as the present application for planning surgery. In these publications, a double scan technique is disclosed, comprising a first CT scan of a jaw region of a patient with a radiographic guide, and possibly a radiographic index inserted in its mouth, as well as a second CT scan of solely the radiographic guide without the radiographic index.

The computer based dual scan technique provides reliable and safe planning and production of a surgical template. However, a CT related issue is that CT scanning sometimes is not capable of accurately representing the oral anatomy. For instance, existing metal based dental restorations in the patient may cause severe scattering during CT scanning. Furthermore, CT scans, which are often repeated during subsequent examinations of the patient, present a substantial load of radiation as the whole skull is exposed to radiation from the CT scanner during the first CT scan. Hence, another issue is that the amount of radiation to which the patient is exposed to during the preparation of data for planning of dental restorative procedures and production of dental restorations and related products is to be minimized.

Moreover, the second CT scan of solely the radiographic guide does sometimes not provide sufficient accurate data so that the surgical template designed in the CAD system from the CT scan data acquired by this second CT scan may in some situations cause a deteriorated patient fit. One reason for this is that CT scan data does not have sufficient data accuracy for producing a dental restoration, such as a coping, abutment, bridge, crown, anatomic abutment, anatomic crown, inlay, onlay, etc. from that CT scan data.

Furthermore, there is still a need for minimizing the number of steps necessary for planning of dental restorative procedures and production of dental restorations and related products.

Hence, an improved system for planning of dental restorative procedures and production of dental restorations and related products, would be advantageous.

SUMMARY

Accordingly, the present disclosure preferably seeks to mitigate, alleviate or eliminate one or more deficiencies, disadvantages or issues in the art by providing a method, system, computer program, and a medical workstation, which are useful for planning a dental restorative procedure of a patient and for producing at least one dental restoration and/or product related to the dental restorative procedure.

The different aspects of the disclosure are recited in the attached independent patent claims.

According to one aspect a method useful for planning a dental restorative procedure of a patient and for producing at least one of a dental restoration and a product related to the dental restorative procedure to be used in said dental restorative procedure is provided. The method comprises matching first data of the patient's craniofacial area from a first data input source with second data of the patient's intra oral anatomy from a second data input source, different from said first data input source, into matched data for said planning and producing, wherein at least a part of said first data in said matched data is provided for said planning and at least a part of said second data in said matched data is provided for said producing.

According to another aspect a system useful for planning a dental restorative procedure of a patient and for producing at least one of a dental restoration and a product related to the dental restorative procedure to be used in said dental restorative procedure is provided. The system comprises a matching unit for matching first data of the patient's craniofacial area from a first data input source with second data of the patient's intra oral anatomy from a second data input source, different from said first data input source, into matched data for said planning and producing, wherein at least a part of said first data in said matched data is provided for said planning and at least a part of said second data in said matched data is provided for said producing.

According to a further aspect of the disclosure, a computer program useful for planning a dental restorative procedure of a patient and for producing at least one of a dental restoration and a product related to the dental restorative procedure to be used in said dental restorative procedure, is provided for processing by a computer. The computer program comprises a code segment for matching first data of the patient's craniofacial area from a first data input source with second data of the patient's intra oral anatomy from a second data input source, different from said first data input source, into matched data for said planning and producing, wherein at least a part of said first data in said matched data is provided for said planning and at least a part of said second data in said matched data is provided for said producing.

According to yet a further aspect of the disclosure, a medical workstation for carrying out the method of the above mentioned aspect of the disclosure by running the computer program of the above mentioned further aspect of the disclosure is provided.

Further embodiments of the disclosure are defined in the dependent claims.

Some embodiments of the disclosure provide for reduced patient dosage.

Some embodiments provide for presurgical planning of a dental restorative procedure and production of dental restorations and/or products related to said dental restorative procedure without the need of preparing a working cast.

Some embodiments eliminate the need for CT scans for providing data for planning of dental restorative procedures or for providing products related thereto.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the disclosure are capable of will be apparent and elucidated from the following description of embodiments of the present disclosure, reference being made to the accompanying drawings, in which

FIGS. 14 to 18 illustrate matching of an intraoral image with high precision 3D scanning data, wherein FIG. 14 illustrates a line through an occlusion;

FIG. 15 illustrates an intraoral image matched to a dental impression from 3D scanning;

FIG. 16 shows the intraoral image;

FIG. 17 is a schematic illustration of pre-surgical planning a dental implant using the intraoral image;

FIG. 18 is a schematic illustration of implant placement planning with the matched intraoral image and scanned dental impression;

DETAILED DESCRIPTION

Figure 1:
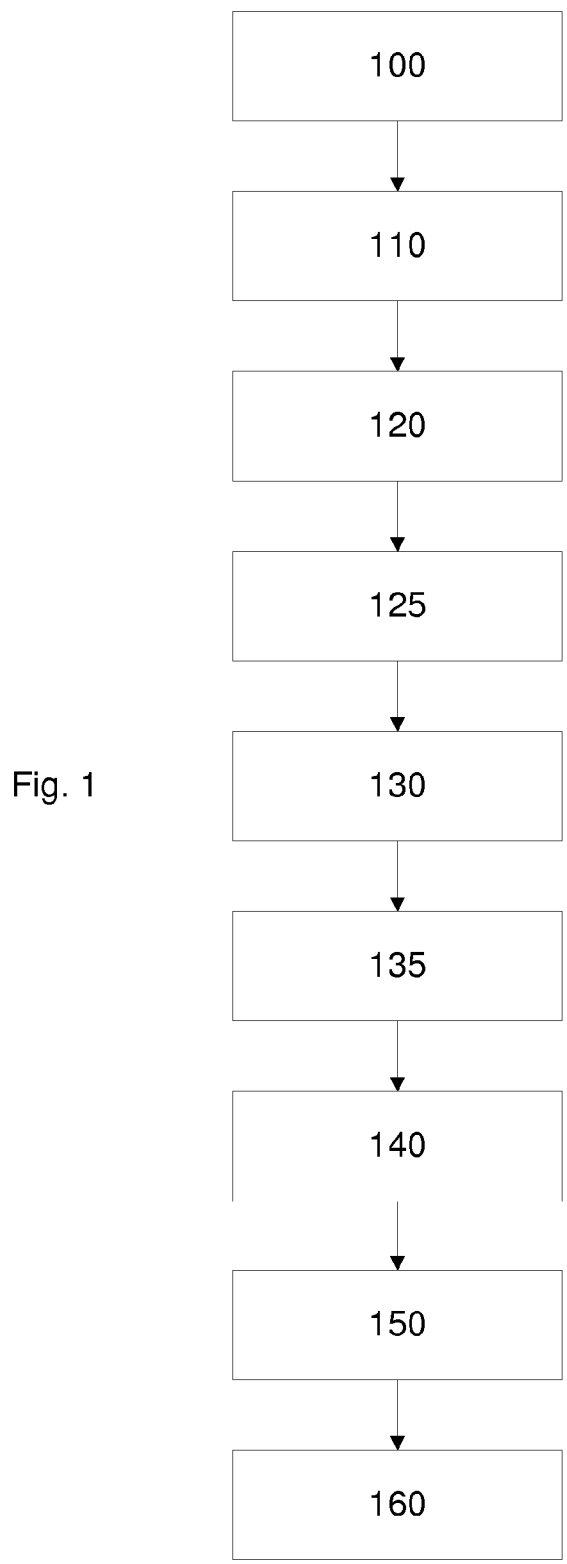
FIG. 1 is a flow chart illustrating planning of dental restorative procedures and production of dental restorations and related products, as well as preparation of data therefor.

Embodiments of the disclosure will now be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. The terminology used in the detailed description of the embodiments illustrated in the accompanying drawings is not intended to be limiting of the disclosure. In the drawings, like numbers refer to like elements.

As mentioned above, systems have been presented in the international applications WO02/053056 and WO2005/055856 of the same applicant as the present application disclosing a double scan. In more detail, the above-mentioned radiographic guide may be used to simulate the teeth, the soft tissue surface and edentulous space during the first CT scan. The radiographic guide is made of an acrylic non radio opaque material, and fabricated in a laboratory from a maxillary impression, a mandibular impression, and a bite registration index taken from the patient. Radio opaque gutta percha markers are inserted in the radiographic guide, providing reference points.

The reason for this double scan technique is that the Hounsfield Units generated for the non radio opaque radiographic guide resemble so closely those of soft tissue. In the first CT scan the patient and the radiographic guide inserted into the oral cavity of the patient are CT scanned. From the data provided by the first CT scan, it is therefore difficult to separate the non radio opaque radiographic guide from the soft tissue of the patient. However, the spatial position of the radiographic guide in the first CT scan may be determined from the radio opaque gutta percha markers. During the second CT scan solely the radiographic guide is CT scanned and CT data is provided for both the radiographic guide and the position of the gutta percha markers. The gutta percha markers on the radiographic guide are used as reference points to perform a match of the first CT scan and the second CT scan. Data from the first and second CT scans are matched and used for computer based planning of a subsequent surgery, including production of a surgical template. The surgical template may be used for creating suitable bores for mounting one or several dental implants to which the dental restorations are fixed.

In FIG. 1 a flow chart is given for the purpose of illustrating an embodiment of an improved method of planning a dental restorative procedure and production of dental restorations and/or related products to the dental restorative procedure, as well as preparation of data therefor. The method may comprise:

100: a dental impression is taken;
110: the dental impression is 3D scanned;
120: the patient is CT scanned with the dental impression inserted in the patient's oral cavity;
125: data from the 3D scanning and data from the CT scanning are matched;
130: a CAD design comprising pre-surgical planning and preparation of production data is made based on the matched data;
135: production of a surgical template;
140: a dental restoration is manufactured;
150: optionally veneering of the dental restoration—the final dental restoration may be completely CAD planned or optionally a manual finishing may be performed;
160: installation of the dental restoration in the patient.

Embodiments of the method will be elucidated in more detail below with reference to FIGS. 2 to 18.

In dental repair applications, an impression is often used to create an imprint or negative likeness of for instance the teeth and adjacent portions of the jaw, such as tooth formations, the contour of the gums, etc. Also, for edentulous patients, an impression of only the gums may be taken. The impression is made preparatory to dental repair or restoration of missing dental structures. Impressions are typically made by placing a soft, semifluid material within the confines of an open trough or channel of an arcuate tray which is then positioned within the mouth of a patient, thus allowing the material to set or cure. To provide the most accurate articulation, the impression cast should represent the entire dental arch. For this purpose, a first tray is used for taking an impression of the upper (maxillary) jaw, a second tray is used for taking an impression of the lower (mandible) jaw, and a bite index is taken by means of a third tray. From the negative or female cast of the teeth and surrounding structures, a positive reproduction or male plaster cast is created for the purpose of fabricating dental restoration, such as inlays, onlays, crowns, bridges, restorations or the like.

Figure 2:
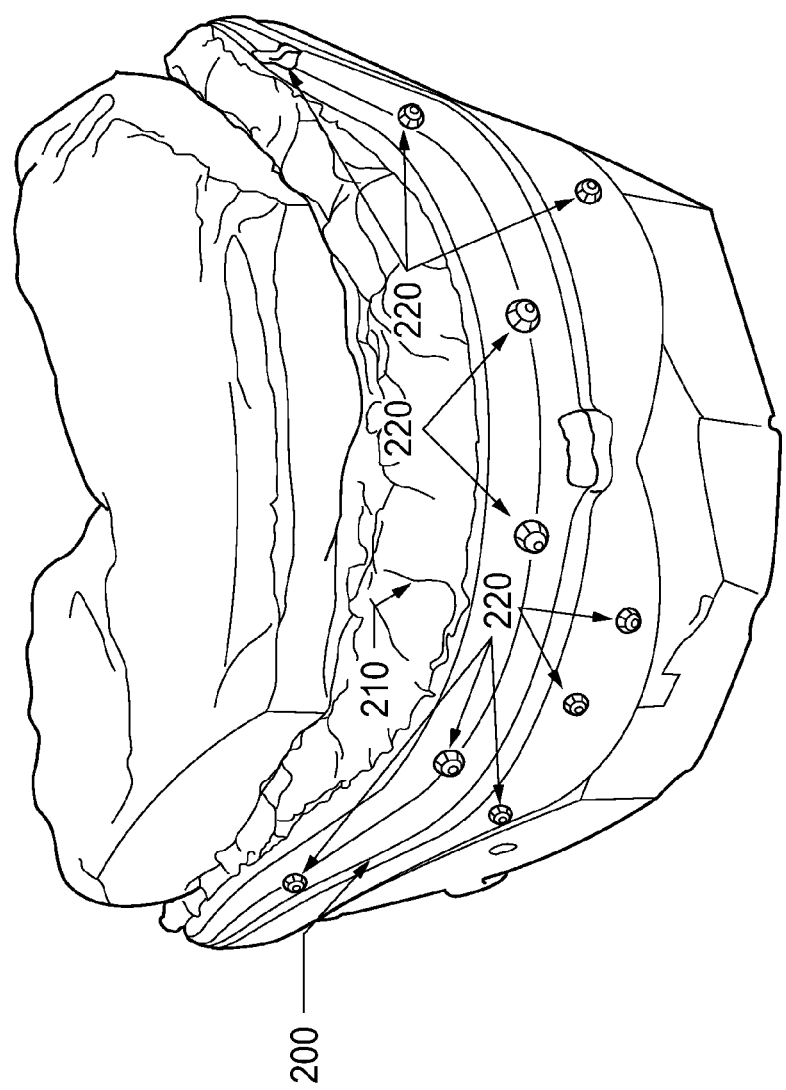
FIG. 2 is a schematic drawing showing a dental impression tray during impression taking with the impression between upper and lower jaw in occlusion and fiducial markers, such as silicon carbide (SiC) spheres, or aluminum oxide (AlO) spheres, in position on the dental impression tray.

Obtaining a dental impression of a patient in step 100 includes filling a suitable amount of a dental impression material 210 into a receiving cavity of a dental impression tray. The dental tray is positioned in a desired location inside the mouth of the patient and the impression is formed in the dental impression material 210 after the patient bites down the impression material in the dental impression tray. FIG. 2 is a schematic drawing showing a dental impression tray 200 during impression taking with the impression material between the upper and lower jaw in occlusion. The dental impression material is let harden in the tray for a suitable period of time after the patient bites down the impression material. Then the dental impression tray 200 is removed from the mouth of the patient. The dental impression may be used with any impression material that is or will be available for recording the patient's intra oral anatomy.

The dental impression tray 200 shown in FIG. 2 is of the triple tray type, allowing obtaining both the mandibular and maxillary impressions in one step, together with the spatial relationship of the two impressions, i.e. the bite registration index. However, according to other embodiments, a single tray, or a plurality of single trays and a bite index, may be used. Also, according to some embodiments, a dental impression tray only partly covering a dental arch may be used, depending on the nature of the dental restoration that is to be planned and produced.

Dental impression tray 200 has fiducial markers, for instance in the form of spheres, in position on the dental impression tray. These fiducial markers are used to define the exact position of the dental impression tray 200 in space, and thus also of the dental impression hold by the dental impression tray.

A suitable dental impression tray is described in Swedish patent application no. SE0602272-7 which is incorporated herein in its entirety by reference, filed by the same applicant as of the present application.

The dental impression tray 200 may be made from a suitable material such as plastics, including polyvinyl chloride, nylon, and high-density polyethylene, e.g. by injection molding.

A frontal handle may ensure convenient handling as well as correct maxillary and mandibular orientation of the dental impression tray 200. Dental impression tray 200 comprises a plurality of fiducial markers 220, wherein the fiducial markers 220 are arranged in a defined relation to at least at one outer surface of the dental impression tray 200 in such a manner that the dental impression tray 200 is in-vivo insertable into the mouth of a patient for impression taking.

The fiducial markers may also be arranged inside the dental impression tray. In this case, the fixed positions of the fiducial markers in relation the surface of dental impression tray may be stored in a CAD model of the dental impression tray. More precisely, positions of the fiducial markers inside the tray may be provided precisely by CAD data of the dental impression tray. 3D scanning of the tray, for instance with a dental impression, then provides data of the outer surface of the tray. By means of the CAD data, the exact position of the fiducial markers inside the dental impression tray is determinable. When imaging the dental tray by means of CT scanning, X-ray etc, the position of the radio opaque fiducial markers is provided although they are arranged inside the tray material, due to the non-radioopacity of suitable tray material. Matching of the CAD tray data with for instance CT scan data enables a reconstruction of the precise positions of the fiducial markers. Matching may be facilitated by a landmark on the surface of the dental impression tray. By means of the CAD model, the spatial relation of the landmark to a fiducial marker may be known. In order to increase determination efficiency further, each fiducial marker may have a specific landmark associated thereto.

Also, in case one or more fiducial markers are lost during CT scanning, e.g. due to artifacts for instance caused by existing metallic fillings in the patient's teeth, the position of these fiducial markers may still be reconstructed. Reconstruction of the position of one or more fiducial markers lost in CT scan data may be based on the position of the above described landmarks.

The dental impression tray 200 may comprise at least three fiducial markers distributed across the tray 200 in order to provide for precise identification of the spatial orientation of the tray 200.

The fiducial markers 220 may partly extend out of at least one outer surface of tray 200, in such a manner that said fiducial markers are identifiable by 3D scanning of said outer surface. The fiducial markers may be identified by their physical shape. For instance, the fiducial markers are a three dimensional object having a specific shape, such as spherical beads. For identifying the fiducial markers, the specific shape of the fiducial marker is searched in a data set. The fiducial markers may be made of a radio opaque material, such as silicon carbide (SiC), aluminum oxide (AlO), or Silicon nitride ($Si_3N_5$), which makes the position of the fiducial markers clear in a radiographic image. Alternatively landmarks related to the fiducial markers in combination with CAD data identification may be used for identifying the fiducial markers.

The dental impression tray 200 may provide for simultaneous impression taking of both upper jaw, lower jaw and bite registration index.

Once the impression material is set, the dental impression tray 200 is removed from the mouth and the impression is available and left in the tray for further handling. After the impression material sets, the impression may be directly 3D scanned in step 110 by means of a high resolution 3D scanner, for instance an optical scanner, such as a laser scanner, a mechanical high precision scanning probe scanner, or a holographic scanner. Commercially available examples for high resolution 3D scanners include OptiMet's 3D non contact scanners based on conoscopic holography technology, or 3Shape's dental 3D scanner. 3Shape's dental 3D scanner uses an optical scanning system, in which laser planes are projected onto the object to be scanned. High-resolution digital cameras acquire images of the lines created on the object. The images are processed and accurate and fully surfaced 3D models may be obtained. A further 3D scanner is available from Renishaw. The Renishaw scanner is a touch probe based digitizing system.

Furthermore, intra oral optical scanners may alternatively be used in order to provide input data for high resolution 3D models of at least a part of the topography of the patient's intra oral anatomy. One such scanner is commercially available from CADENT. Matching is in this case solved differently, see below, as the intra oral scan does not provide data from fiducial markers on a dental impression tray during intra oral scanning. One way of matching is for instance to attach fiducial markers appropriately to anatomical structures in the intra oral anatomy of the patient, such as on possibly existing teeth of the patient. Intra oral 3D scanning the intra oral anatomy provides data for identifying the fiducial markers on the teeth in the 3D data set obtained, by finding the shape of these fiducial markers. Thus position data for the fiducial markers is provided that may be matched with craniofacial data. Craniofacial data may for instance be obtained by CT scanning with the fiducial markers on the teeth. The radio opaque fiducial markers are identified in the CT data set, providing the position thereof. Matching of the 3D data set with the CT data set is made by means of the identified positions of the fiducial markers.

An alternative way is to use surface matching. Surfaces may be identified in both CT data and 3D data. For instance a number of surfaces of teeth may be identified by suitable algorithms. CT data may be converted to a surface model of the intra oral anatomy. A tooth or several teeth and surfaces thereof, or an occlusion surface may be identified in the CT data. Correspondingly, surfaces are identifiable in 3D data. CT data and 3D data is then matched by using the identified surfaces in both data sets.

A further alternative way is to use contour matching. Contours may be identified in both CT data and 3D data. For instance a contour of a tooth or several teeth may be identified by suitable algorithms. CT data and 3D data is then matched by using the identified contours in both data sets. In some embodiments surface matching and contour matching methods may be used in combination. Surface matching and contour matching methods may be used alternatively to or in combination with fiducial markers.

Figure 3:
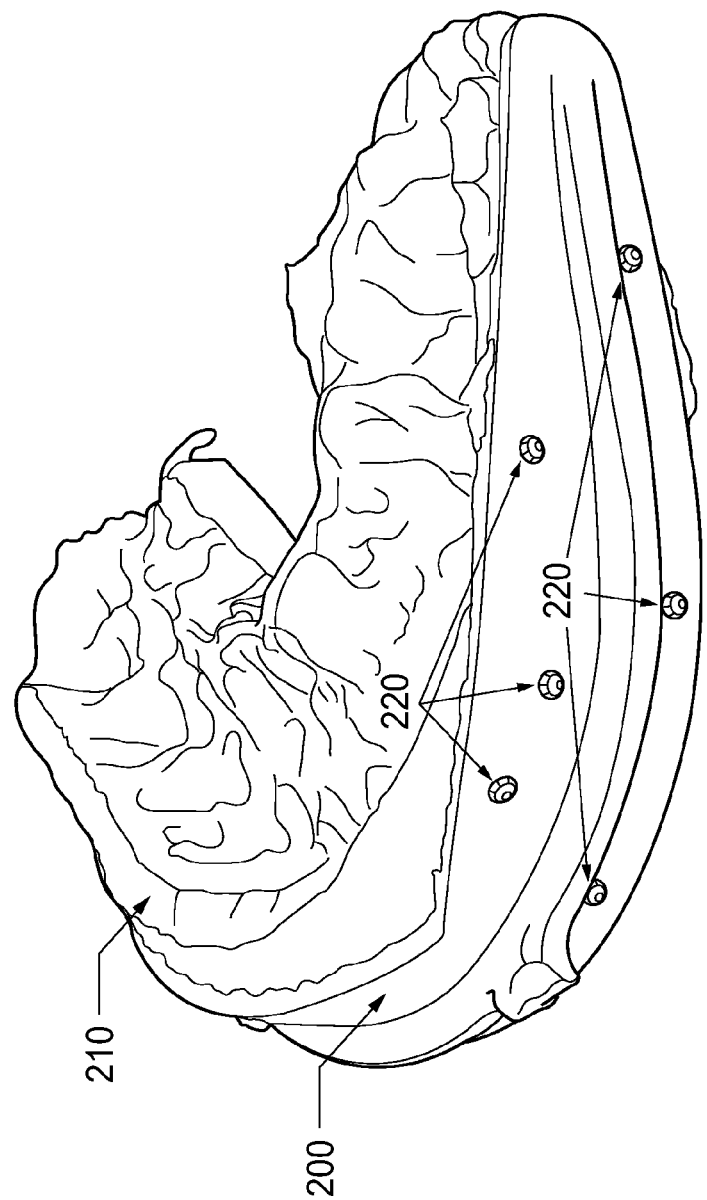
FIG. 3 is a schematic drawing in a perspective view showing the dental impression tray with the impression taken, wherein the impression with fiducial markers, such as silicon carbide (SiC) spheres, is in position for matching.

FIG. 3 is a schematic drawing in a perspective view showing the dental impression tray 200 with the impression of both jaws taken, wherein the impression with fiducial markers is in position for matching.

Figure 4:
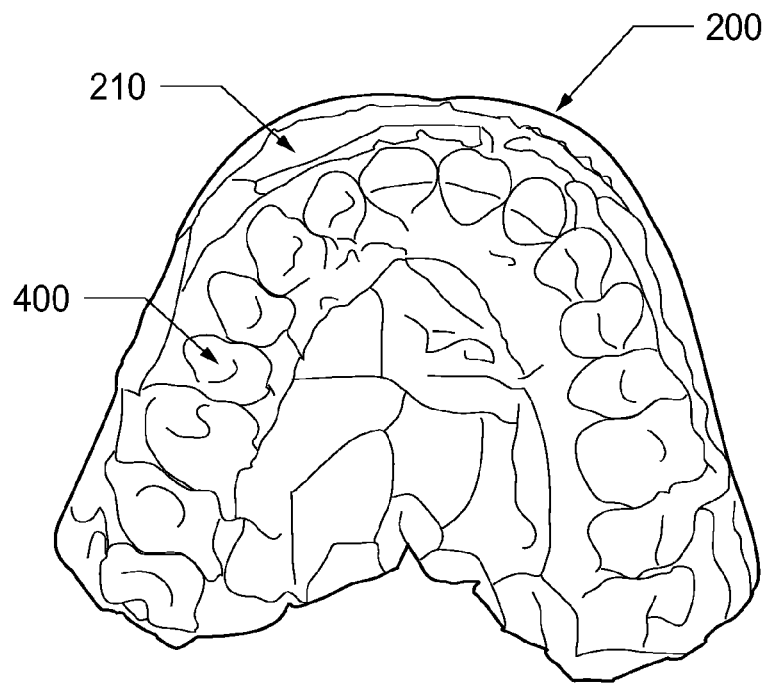
FIG. 4 is planar view taken from above of the dental impression tray with the impression taken of FIG. 3 showing the impression of the upper jaw.

FIG. 4 is planar view taken from above of the dental impression tray 200 with the impression taken of FIG. 3 showing the impression 400 of the upper jaw.

Figure 5:
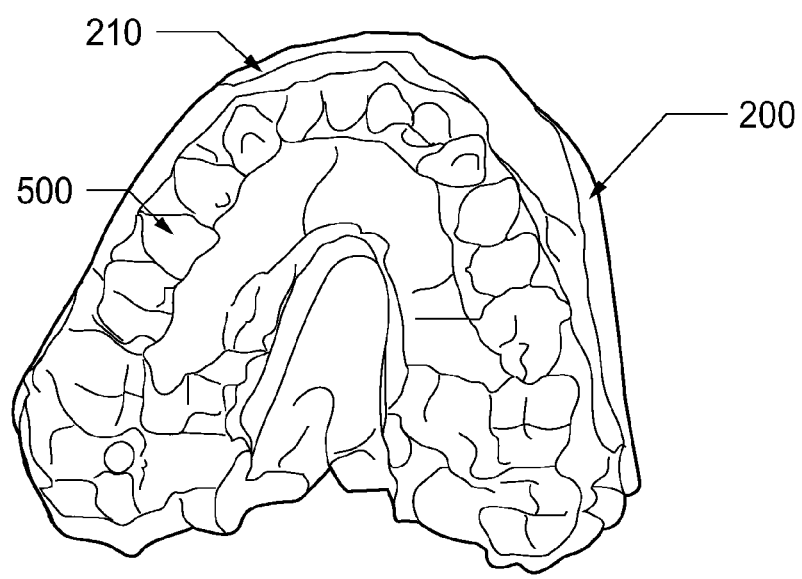
FIG. 5 is planar view taken from below of the dental impression tray with the impression taken of FIG. 3 showing the impression of the lower jaw, opposite the impression of the upper jaw shown in FIG. 4.

FIG. 5 is planar view taken from below of the dental impression tray 200 with the impression taken of FIG. 3 showing the impression 500 of the lower jaw, opposite the impression 400 of the upper jaw shown in FIG. 4.

When at least one dental impression is obtained, for instance as described above, the hardened dental impression is digitized, e.g. by means of a non-contact 3D surface scanner. For instance, the above-described dental impressions of the upper and lower jaw in tray 200 with the fiducial markers 220 are scanned using a 3D scanner of the above-described type, such as a 3D laser surface scanner. The measurements made by such 3D scanners are very precise and virtually eliminate an operator error because the acquisition of data is automatic.

The accuracy of a 3D scanner is in the range of tens of microns, for instance 10 to 50 microns, i.e. 0.01 to 0.05 mm, such as 20 or 30 microns. This resolution of the 3D scanner is magnitudes finer than that of a CT scanner. A CT scan has an accuracy in the region of 0.5 to 1 mm. Some more detailed specific resolutions for CT scanners as well as for 3D scanners are given below in table 1. Hence, by using a 3D scanner, for instance an optical scanner, such as a laser scanner, high resolution data of the topography of the patient's intra oral anatomy, possibly comprising the patient's remaining dentition, is provided for computer based dental planning of dental restorative procedures and for production of dental restorations and/or products related to the planning of dental restorative procedures.

Previously, this data was obtained from 3D scanning the above-described plaster cast.

TABLE 1

Comparison of different CT scanner's and 3D scanner's precision

| | CT (Single Slice) | CT (Multi Slice) | Conebeam |
|---|---|---|---|
| Slice Thickness Scanning | 1 mm | 0.7 mm | |
| Slice Thickness Reconstruction | 0.1 mm-0.5 mm | 0.1-0.5 mm | 0.125-0.5 mm |
| Scanner's Precision | 3Shape (Optical) | Optimet (Optical) | Renishaw (Probe) |
| | 20-30 microns | 10-30 microns | 3-20 microns |

In another embodiment, each side of the impression, i.e. the upper jaw impression and the lower jaw impression, is 3D scanned separately. In another embodiment both impressions are 3D scanned together or concurrently.

Figure 6:
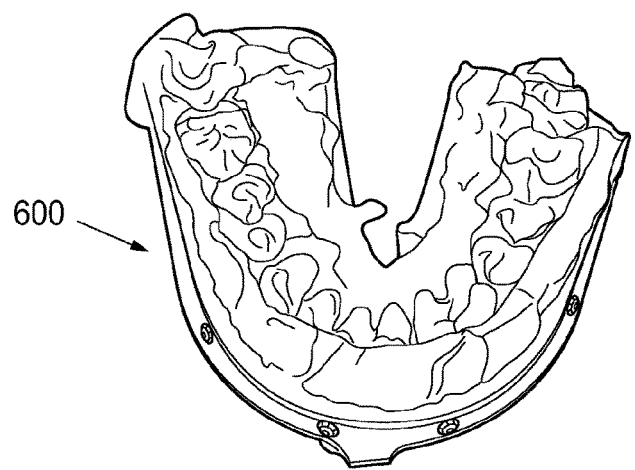
FIG. 6 is a schematic drawing in a perspective view showing a rendered computer visualization of a 3D model obtained from optical scanning of the impressions of the upper and the lower jaw in the dental impression tray of FIG. 3, digitized to a CAD Software with high precision, such as a resolution of 30 microns.

FIG. 6 is a schematic drawing in a perspective view showing a rendered computer visualization 600 of a 3D model impression data obtained from the optical scanning of the impressions of the upper and the lower jaw in the dental impression tray of FIG. 3. By means of a computer program, one or more scanned negative dental impressions may be turned inside out to generate one or more positive models of the dentition. In this way a 3D digital dental model may be created.

After the dental impressions in the dental impression tray are prepared, and 3D scanning of the impressions is terminated, the dental impressions in the dental impression tray 200 with fiducial markers 220 are again placed into the maxillary and mandibular jaws of the patient in step 120. The patient with the inserted dental impression tray 200 is then CT scanned. The patient bites with the impression in position during performing the CT scan. Digital CT data is thus provided comprising craniofacial data and fiducial markers.

The digital CT data are now available for further processing. A 3D craniofacial model is then reconstructed based on CT data. Position of fiducial markers 220 are acquired and registered, for instance for use in a matching algorithm using the position of the fiducial markers 220.

The resolution of the 3D CT dentition model is in the range of 0.5 to 1 mm. With this accuracy, surgical planning is now possible. According to an embodiment, surgical planning is positioning of a dental implant. However, it is not possible to accurately produce a dental restoration from the CT data to the degree that is desired. For instance, the occlusion between maxillary and mandibular teeth requires a high degree of precision of the fitting of a dental restoration into the existing dentition and/or dental implants; even a small error may result in malocclusion. Some production tolerances for dental restorations are recited in table 2. The mentioned ranges for the production tolerances ensure a reliable long-term dental restoration, ensuring satisfied patients.

TABLE 2

Production tolerances for various dental restorations

| | Abutment | Coping | Bridge (Screw Retained) | Bridge (Cemented) |
|---|---|---|---|---|
| Production Tolerances | 5-100 Microns | 5-100 Microns | 5-100 Microns | 5-150 Microns |

In step 125 data from 3D scanning and data from CT scanning is matched. Matching of high resolution 3D scan data with CT scan data into matched data provides for surgical planning and production of a dental restoration or product related to said dental restoration, such as a surgical template, from that single set of matched data. This means that planning of a dental restorative procedure and providing of data for production of the products used therefore may be made in a single medical workstation in a continuous workflow at the same occasion. At the same time high precision and reliability of the products used provides for reliable and safe results of dental restorative procedures.

The medical workstation 1910 comprises the usual computer components like a central processing unit (CPU) 1920, memory 1930, interfaces 1940, etc. Moreover, it is equipped with appropriate software for processing data received from data input sources, such as data obtained from CT scanning or 3D scanning. The software may for instance be stored on a computer readable medium 1930 accessible by the medical workstation 1910. The computer readable medium 1930 may comprise the software in form of a computer program 1940 comprising suitable code segments for planning a dental restorative procedure of a patient and for producing at least one of a dental restoration and a product related to the dental restorative procedure. For example, the computer program 1940 may include a code segment, or a matching unit 1945, for matching first data of the patient's craniofacial area from a first data input source with second data of the patient's intra oral anatomy from a second data input source into matched data for planning and/or for producing a dental restoration. The medical workstation 1910 further comprises a monitor 1922, for instance for the display of rendered visualizations, as well as suitable human interface devices 1924, like a keyboard, mouse, etc. The medical workstation may be part of a system 1900 for planning a dental restorative procedure of a patient and for producing at least one of a dental restoration and a product related to the dental restorative procedure.

For matching, the 3D CT dentition model is imported into a software for pre-surgical planning of dental restorative procedures, for instance run on the medical workstation 1910. When the pre-surgical planning is made, production of dental restorations and/or products related to said pre-surgical planning, such as surgical templates, may be made.

More precisely, matching of the CT data set and the 3D scanned data set may be performed as follows. A portion of the 3D CT dentition model is removed, e.g. teeth, soft tissue or gums. The positions of the fiducial markers 220 in the CT data set are acquired for matching with the position of the same fiducial markers 220 in the 3D digital dental data acquired by 3D scanning. The positions of the fiducial markers in the CT data set may be determined by searching for the specific form of the radio opaque fiducial markers in the CT data set. When a fiducial marker is identified in the CT data set, its position is thus known. The position of fiducial markers in the 3D data set may be determined by searching for the specific form of the fiducial markers in the 3D data set, in case the fiducial markers are only partly embedded into the surface of the dental impression tray. Here, the shape of the fiducial markers is searched in the 3D data set, and when found, the position of fiducial markers is known. In case one or more fiducial markers are completely embedded into the material of the dental impression tray, landmarks in combination with CAD data of the dental impression tray may be used for determining the position of the fiducial markers. In this case, the shape of the landmarks is searched in the 3D data set and when found, the position thereof is known. By linking the position of the landmarks to the position of the fiducial markers via the CAD data, also the position of the fiducial markers in the 3D data set is known.

The 3D data and the CT data are matched by aligning the fiducial markers 220 of the dental impression tray 200. More precisely, the fiducial markers 220 of the CT data are matched with the same fiducial markers 220 of the corresponding 3D data. The positions of the fiducial markers in relation to the remaining structure of the dental impression tray are known, e.g. from the CT scan data, from CAD data of the dental impression tray, etc. Matching of the CT data with 3D scan data is thus made.

A computerized composite dental model is created, in which the bone structure is based on CT scanning, and in which the dental structure is based on high resolution optical scanning. In this manner surgical planning is enabled with sufficient precision based on the 3D CT data. Production of dental restorations and/or products related to the surgical planning, such as a surgical template, is enabled with sufficient precision based on the high precision 3D scanning data. This means that based on the matched data that is available now, both planning and production are provided from one data set, namely the matched data set, without the necessity of any further collection of data, preparation of plaster casts, etc.

Figure 7:
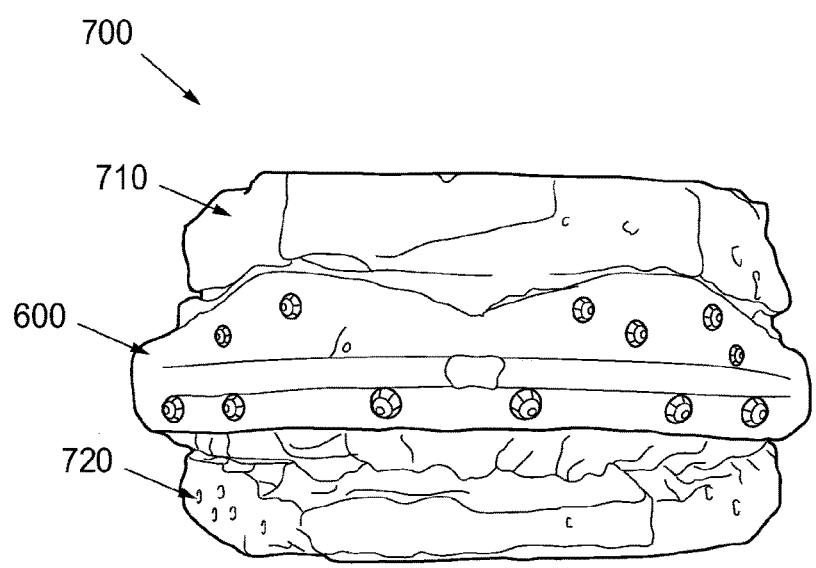
FIG. 7 is a schematic drawing in a front view showing a rendered computer visualization of the computerized 3D model of the dental impression tray and impression of FIG. 3, from a CT scan of the patient and the dental impression tray and impression inserted in the patient's mouth, wherein the patient bites with the impression in position and then a CT scan is performed.

FIG. 7 is a schematic drawing in a front view showing a rendered computer visualization 700 of matched data from the dental impression tray and impression of FIG. 6, inserted in the patient's mouth. The rendered computer visualization 700 shows the upper jaw 710, the lower jaw 720 and the dental impression tray 600.

Figure 8:
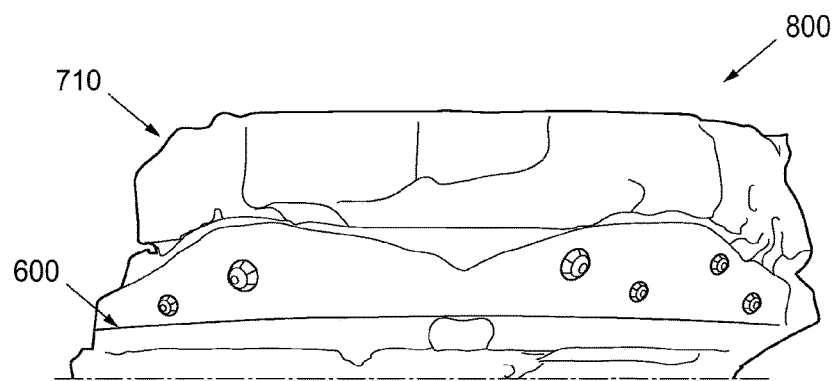
FIG. 8 is a schematic drawing in a front view showing a rendered computer visualization of the CT scanned patient's upper jaw and matched with 3D data of the optically scanned impression.

FIG. 8 is a schematic drawing in a front view showing a detail from FIG. 7, namely a rendered computer visualization 800 of the computerized composite dental model. The CT scanned patient's upper jaw 710 is matched with 3D scan data of the 3D scanned impression.

Figure 9:
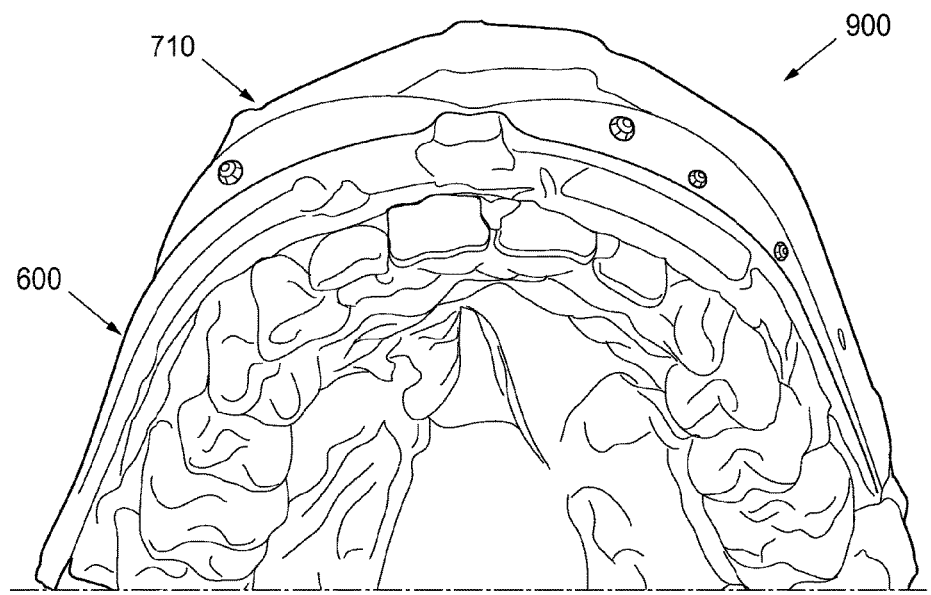
FIG. 9 is a schematic drawing in a perspective view from frontally below, showing a rendered computer visualization of the CT scanned patient's upper jaw and matched with 3D data of the optically scanned impression.

FIG. 9 is a further schematic drawing in a perspective view from frontally below, showing a rendered computer visualization 900 of the computerized composite dental model. The CT scanned patient's upper jaw is matched with 3D data of the optically scanned impression.

Figure 10:
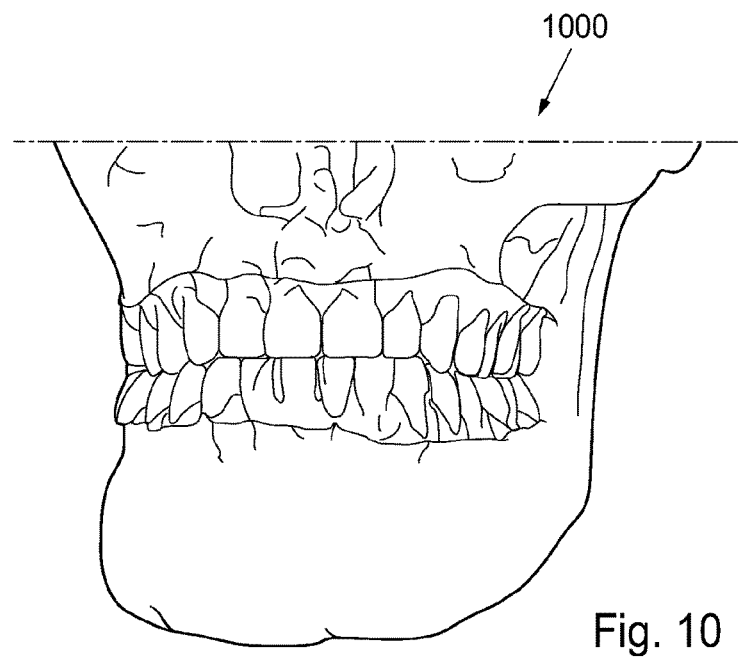
FIG. 10 is a schematic drawing in a frontally taken perspective view, showing a rendered computer visualization of the patient's craniofacial CT scan matched with the 3D data received from optically scanning the upper jaw impression and lower jaw impression.

FIG. 10 is a schematic drawing in a frontally taken perspective view, showing a rendered computer visualization 1000 of the computerized composite dental model, wherein the patient's craniofacial CT scan data is matched with the 3D data obtained from optically scanning the upper jaw impression and lower jaw impression.

Now, in step 120 of the method, the presurgical planning is done in the software for computer based dental planning of dental restorative procedures. By using the composite dental model, the plaster model is no longer necessary. Furthermore no separate scan of a radiographic guide is necessary. Thanks to the design of the dental impression tray with fiducial markers, easy clinical use of computer based dental planning of dental restorative procedures, in step 130, are provided. The composite dental model may be used for computer based planning of a subsequent surgery, including production of a surgical template in step 135 of the method. In more detail, the presurgical planning is made computer based in an interactive way. Planning of the dental restoration is made visually on a display of the workstation, in an interactive way manipulated by user input. For instance the position and direction of dental implants in jaw bone is virtually planned on the display visualizing the jaw bone structure where a dental restoration is to be made, based on CT data. During planning care has to be taken that for instance no nerves are damaged or that the dental implant is positioned in as much dense bone as possible, in order to ensure a successful surgical installation of the dental implant. Then a superstructure that will be attached to the implant may virtually be designed, matching the already planned implant, based on 3D scanned data. Hence, the user may create bridges, copings etc. in combination with implant planning in advance of placement.

Based on this presurgical planning, a surgical template may be fabricated using rapid prototyping techniques in step 135. The surgical template is produced with high precision based on the 3D scanned data. The surgical template is used in a known way for creating suitable bores for mounting of dental implants, to which the dental restorations will be fixed, at the planned position and with the planned orientation. Data for products produced by stereolithography, such as a surgical template, may be saved in a suitable format, such as STL. STL (Standard Tessellation Language) files may be imported and exported by a variety of software packages. The STL file is especially suitable for rapid prototyping. This format approximates the surfaces of a solid model with triangles for rapid prototyping. Rapid prototyping takes virtual designs from computer aided design (CAD), transforms them into cross sections, still virtual, and then creates each cross section in physical space, one after the next until the model is finished. STL files generated from CT scans with relatively low resolution often lead to a stepped model when made by rapid prototyping. STL files generated from high resolution optical scans lead to models virtually without any difference from the original. Hence, surgical templates with higher resolution are provided, avoiding a stair effect from rapid prototyping. A typical resolution for rapid prototyping today is in the range of 0.05-0.125 mm. Future resolutions are foreseen to be in the range of 0.005 mm. The present system and method will meet such future higher resolutions of rapid prototyping.

Figure 11:
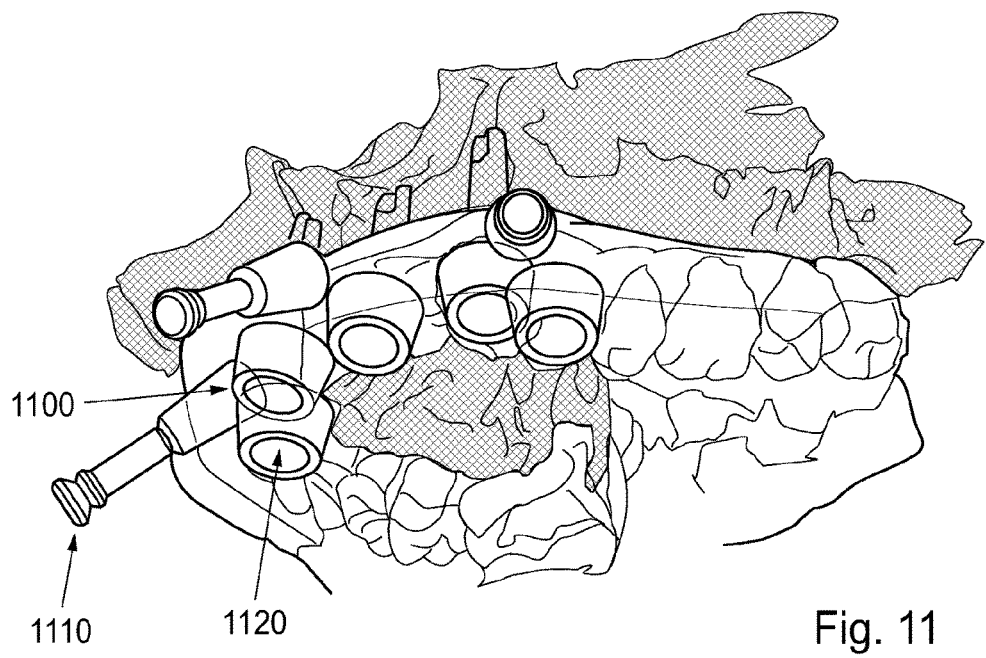
FIG. 11 is a schematic drawing in a perspective view from frontally below, showing matched optically scanned and CT scanned data with surgical planning in a computer based software, such as Procera®.

Other products may be represented by other formats. For instance a data format used for representing copings or bridges is known by the abbreviation TRM. FIG. 11 is a schematic drawing in a perspective view from frontally below, showing matched optically scanned and CT scanned data with surgical planning template 1100 in a computer based software, such as Procera®. Anchoring pins 1110 and guide sleeves 1120 for guiding of drills are schematically illustrated in FIG. 11.

In step 130 of the method, a physical patient model may be manufactured. The patient model may be provided from the data available, if so desired. A patient model may for instance be used for veneering, in case veneering is desired to be performed manually. Production of a patient model and an articulator are described in Swedish patent applications nos. SE 0602271-9 and SE 0602273-5 which are incorporated herein in their entirety by reference, filed by the same applicant as of the present application. However, this step may be omitted, as the available data provides sufficient precision for both presurgical planning and production of surgical templates and dental restorations.

In step 140 of the method, a dental restoration is manufactured based on the high resolution 3D data available. As high resolution data is available from the 3D scanning of the dental impression, the dental restoration is produced directly from that data considering the input made during presurgical planning.

In step 150 of the method, veneering of the dental restoration may be performed in a conventional way. For this purpose the physical patient model mentioned above may be used. In another embodiment design of the final restoration is made virtually based on the high resolution data, whereby manual veneering is no longer necessary.

Finally, in step 160 of the method, the dental restoration is installed in the patient. More precisely, the surgical template produced as described above, is used for providing one or more bores, each receiving a dental implant. Thanks to the high precision with which the surgical template is produced, dental implants are fitted very precise into the jaw bone tissue. Thus a thorough basis is provided for the dental restoration that is then attached to the dental implant in a known manner.

By using the above described method, no casting, sectionizing and pinning of a plaster model is needed. This provides for faster turnaround times when planning and carrying out dental restorative procedures.

Hence, a very precise positioned dental restoration is provided in a very economical and time saving manner.

In some treatments even the surgical template is no longer necessary. For instance when producing a coping, such as for a crown or a bridge, to be attached to a dental preparation, the coping may be produced directly from the high precision input data of the dental tray 3D scanning.

Moreover, as a consequence of the above mentioned high-resolution scanning, instead of the above described CT scan of the complete dentition, a CT scan of a limited area may be used in order to further reduce radiation load on the patient. The limited area may be solely the area into which a dental implant is to be installed. This has hitherto been difficult to implement as CT scans of limited areas of the dentition did not supply sufficient data for producing suitable surgical templates. This is on the one hand caused by the low resolution of CT data, which leads to deteriorated patient fit. On the other hand a surgical template based on a limited area is often not sufficiently stable for reliable surgery. For example, a low dosage conebeam scanner, as manufactured by Morita, only covers a small area, like four centimeters, which results in a surgical template not stable enough for a reliable operation, if solely based on the CT data produced from such CT scanners. However, the data from the conebeam scan is sufficient for planning positioning of an implant.

Figure 12:
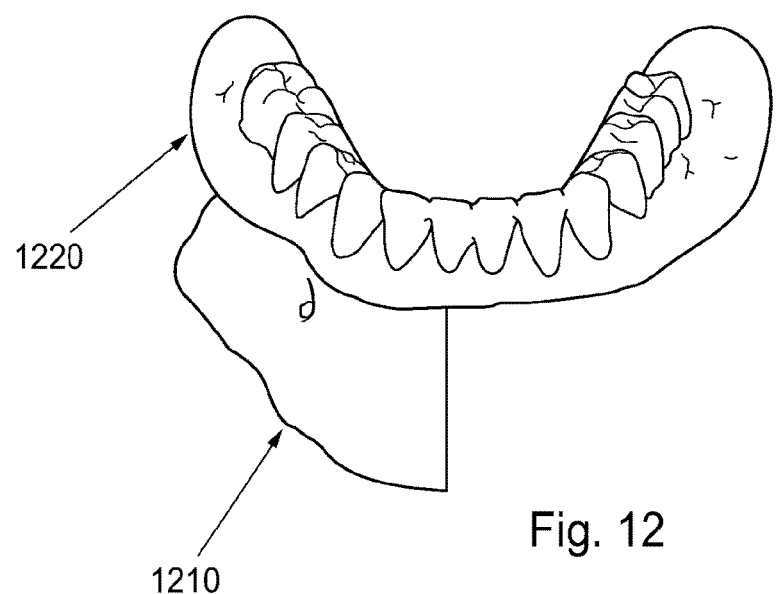
FIG. 12 is a schematic drawing showing rendered computer visualizations, derived from matched CT data of a limited jaw area, such as from a low dosage conebeam CT scanner, and data provided by a high precision 3D scanner derived from scanning a dental impression of an entire dental arch.
Figure 13:
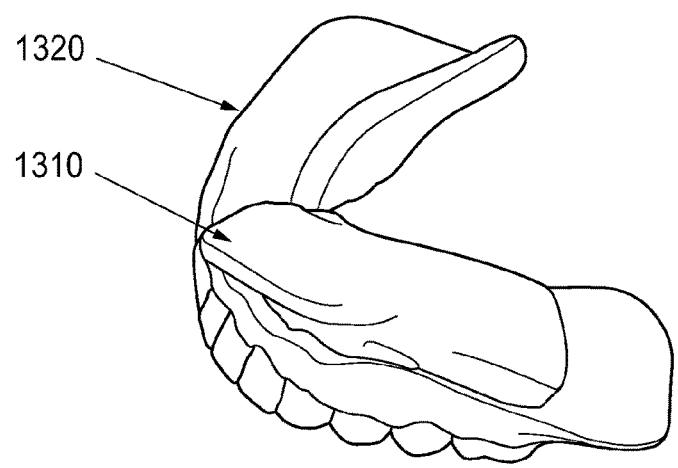
FIG. 13 is a different view of the schematic drawing of a rendered computer visualization of FIG. 12, derived from matched CT data of a limited jaw area, such as from a low dosage conebeam CT scanner, and data provided by a high precision 3D scanner derived from scanning a dental impression of an entire dental arch.

By using data from a 3D scanner of a dental impression in combination with a CT scan of a limited area, e.g. a low dosage CT scanner, it is now achievable to provide surgical templates sufficiently precise and stable and delivering reliable results. Pre-surgical planning of the position and orientation of a dental implant may be based on the data from the CT scan of a limited area, as illustrated in FIGS. 12 and 13. The first data derived from a CT scan provides sufficient information for this purpose, such as jaw bone position and density, extension of nerve channels to be avoided, etc. Furthermore, the high precision scan of a dental impression provides sufficient second data for producing a surgical template that may be attached to intra oral areas that extend beyond the coverage of the limited area scanned by means of the CT scanner. This has previously not been possible. The two data sets are matched to each other, as described above. More precisely, FIG. 12 is schematic drawings showing a rendered computer visualization frontally of a lower jaw 1210 and a dental impression 1220. The interspace between the lower jaw 1210 and the matched data of the dental impression 1220 is of soft tissue, not illustrated herein. FIG. 13 is schematic drawings showing a rendered computer visualization frontally of an upper jaw 1310 and a dental impression 1320. The rendered visualizations are derived from matched CT data of a limited jaw area, illustrated at 1210 or 1310 respectively, such as from a low dosage conebeam CT scanner, and data provided by a high precision 3D scanner derived from scanning a dental impression of an entire dental arch, illustrated at 1220 or 1320 respectively.

Various CT-scanners may be used in combination with a 3D scanner for scanning a dental impression, such as an optical 3D scanner. Some commercially available CT scanners are for instance: Planmeca Promax 3D, Newton 9000 and 3G, I-CAT, Accuitomo Morita. The data from 3D scanning the entire dental arch compensates for non-complete CT scans of the dental arch. It has proven to be sufficient for surgical planning that the bone structure of the jaw in the proximity of the area into which a dental restoration is to be installed is CT scanned, as long as sufficient data is available from the 3D scanning of the dental impression for being able to reliably produce the surgical template.

Figure 14:
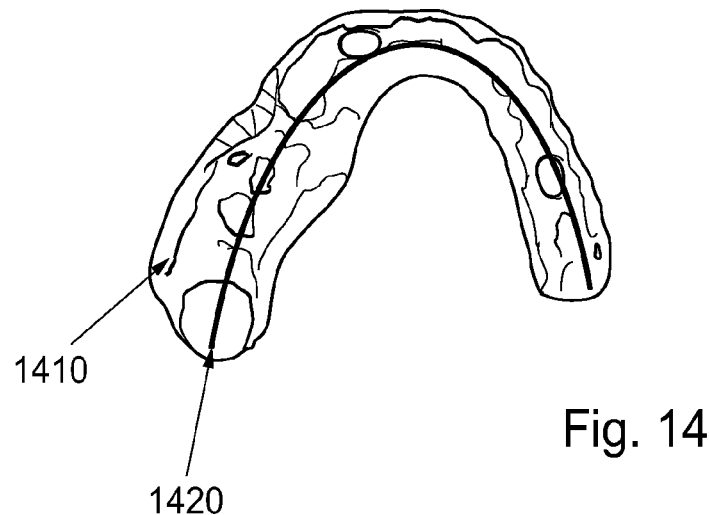

Furthermore, in one embodiment conventional 2D dental X-rays may be matched with the data from the high resolution impression scanning. For instance an intraoral X-ray image showing a segment of a patient's dentition, may be matched with the data from the high resolution impression scanning. The matched input data from the two data sources is sufficient for a variety of dental restoration procedures. The precise position of the data from the high resolution impression scanning may be matched sufficiently accurate with the intra oral X-ray image by using a line through the occlusion. This is illustrated in FIGS. 14 to 18, which illustrate matching of an intraoral image with high precision 3D scanning data. FIG. 14 illustrates a line 1420 through an occlusion of a visualized dental impression 1410 derived from 3D scanning. A two dimensional (2D) contour is generated from X-ray data, following for instance the contour of a tooth. A 2D section of the 3D data from the dental impression is made. The 2D contour is then searched in the 2D section of the impression data. Matching is made by identifying the 2D contour both in the X-ray data set and the section of the 3D data set. Preferably the 2D section is made in the center of the impression along the dental arch, as the 2D X-ray often is taken along the center line of a tooth.

Figure 15:
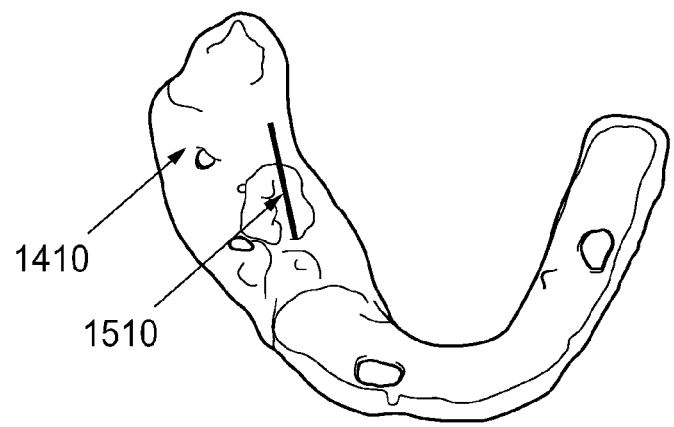
Figure 16:
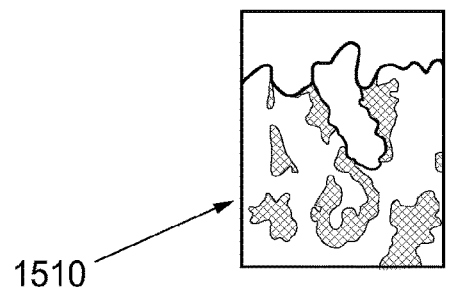
Figure 17:
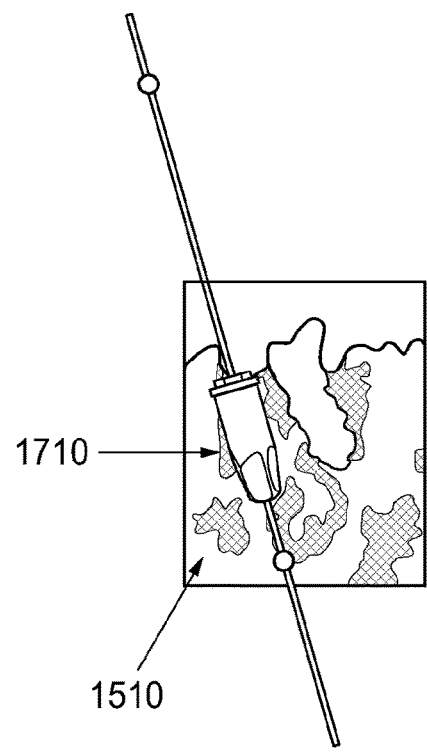
Figure 18:
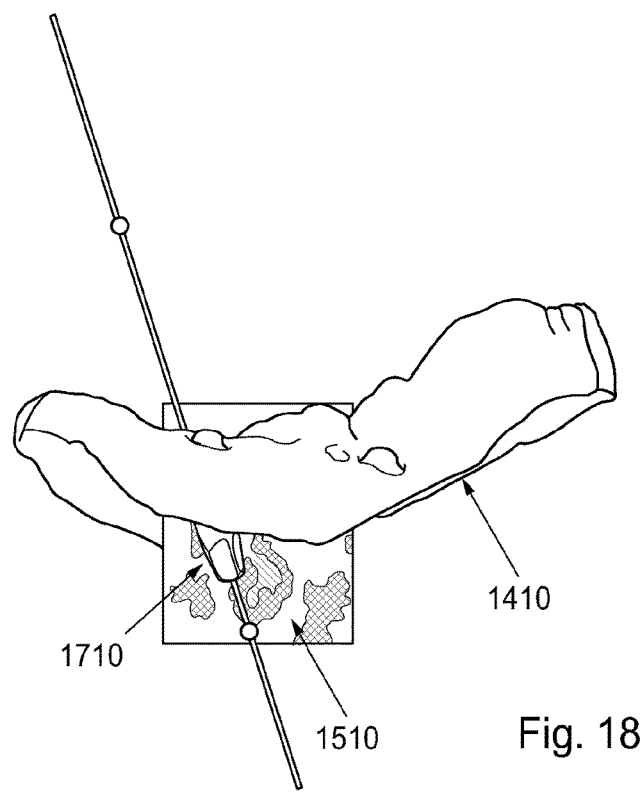
Figure 19:
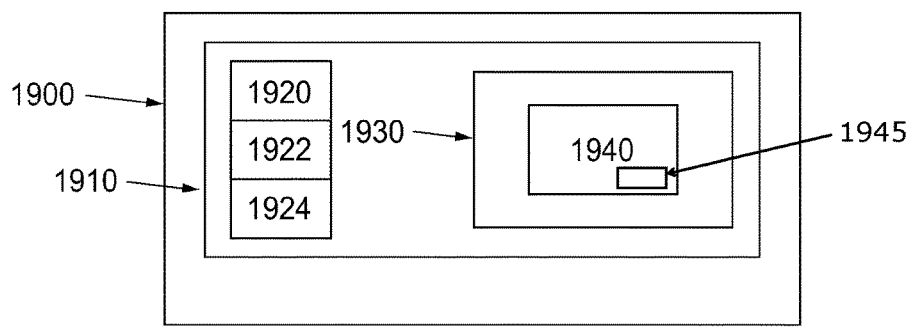
FIG. 19 is a schematic illustration of a system according to an embodiment comprising a medical workstation for executing computer programs.

FIG. 15 illustrates in 3D an intraoral image 1510 matched to the visualized dental impression 1410 from 3D scanning. FIG. 16 shows the intraoral image in 2D. FIG. 17 is a schematic illustration of pre-surgical planning a dental implant 1710 using the intraoral image 1510. FIG. 18 is a schematic illustration of implant placement planning with the matched intraoral image 1510 and the visualized scanned dental impression 1410, as well as the planned implant 1710. FIG. 18 illustrates the pre-surgical planning of the dental restoration procedure to follow thereafter. Production of the implant, surgical template etc. is done as described above based on said matching.

Figure 20A:
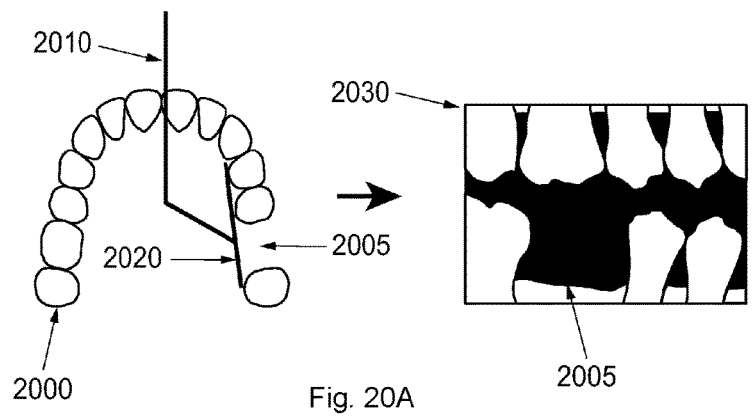
FIG. 20A is a schematic illustration of an example of matching 2D X-ray data with 3D data from a scanned dental impression at a tooth gap.
Figure 20B:
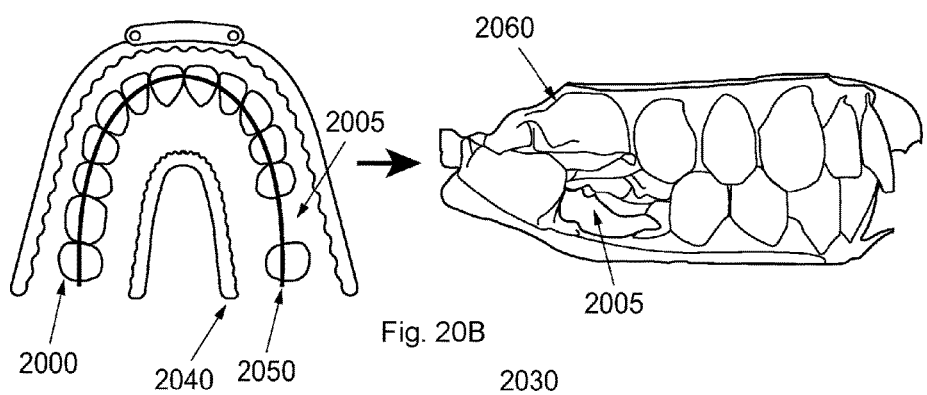
FIG. 20B is a schematic illustration of an example of matching 2D X-ray data with 3D data from a scanned dental impression on a right side.
Figure 20C:
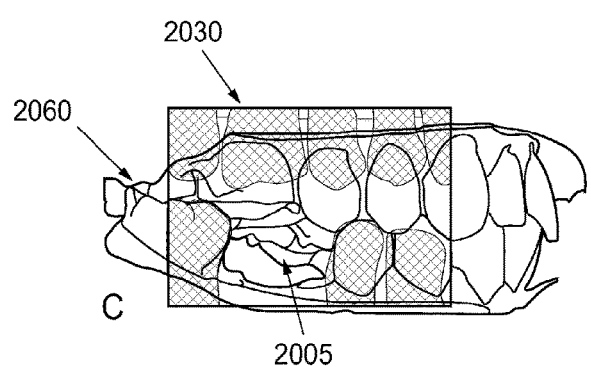
FIG. 20C is a schematic illustration of an example of matching 2D X-ray data with 3D data from a scanned dental impression and jaw bone tissue at a tooth gap.

Another example of matching 2D X-ray data with 3D data from a scanned impression is given in FIG. 20, further elucidating the method illustrated with reference to FIGS. 14 to 18. It is desired to position a dental restoration should be at a tooth gap 2005 of a dental arch having a missing tooth by. For this purpose 2D X-ray data is generated, 3D scanning data of a dental impression is generated, and the 2D data and the 3D data are matched. The matched data may be used for planning of a dental restorative procedure, e.g. planning the position of a suitable implant and dental restoration, as well as for providing data from the planning for production of suitable dental restorations. In more detail, a X-ray image 2030 of the dental arch 2000 at the tooth gap 2005 is taken, as illustrated in FIG. 20A. An X-ray sensitive film plate is illustrated with reference sign 2020. The film plate is hold by a carrier 2010 for convenient insertion into the mouth of the patient. Alternatively, a digital X-ray receiver may be used for registering the X-ray image. The gap 2005 is clearly identifiable in the X-ray image 2030 between two adjacent teeth of the dental arch of the lower jaw. A dental impression tray 2040 is used to take a dental impression of the dental arch 2000. 3D data of the dental arch 2000 is obtained by 3D scanning of the dental impression obtained. A visualization 2060 based on the 3D data is depicted in FIG. 20B on the right side thereof. Also here, the tooth gap 2005 is clearly identifiable. The centerline 2050 of the dental arch 2000 is also illustrated in FIG. 20B. The X-ray image is preferably taken in a direction perpendicular to a plane parallel to the teeth and perpendicular to the centerline 2050. The 2D x-ray data is now matched with the 3D data, which is illustrated in FIG. 20C. 2D X-ray data is for instance matched with the 3D data by contour matching. For instance the contour of a cut through the 3D data dental arch gives a 2D cutplane. The 2D X-ray image may be taken in the same plane as this cutplane. Thus a contour of for instance the two teeth adjacent to the tooth gap 2005 may be matched to the X-ray image in the cutplane. Tooth gap 2005, and matched adjacent teeth, as well as jaw bone tissue of the lower jaw at the site of the tooth gap 2005 are identifiable in FIG. 20C. Based on this matched data, planning may be performed as described above. Possibly more jaw bone may be shown in other X-ray images than the illustrated in order to facilitate planning, if so desired.

By matching input data from different input sources, such as CT scans, X-ray images, and high resolution 3D scanners, it is provided that the radiation dosage to which the patient is exposed to may be reduced. For instance a CT scanner tube may be used with less radiation effect, although resolution of the CT scan is decreased and signal to noise ratio of the CT scan is increased. Radiation dosage to which the patient is exposed to, is lowered. As long as sufficient data for presurgical planning is provided by the CT scan, reliable presurgical planning is enabled from the CT data or X-ray data obtained with reduced patient dosage needed for reliable planning and production. For instance, in case the jaw structure and eventually remaining dentition, and the fiducial markers are sufficiently identifiable in the CT data, a reliable treatment may be provided. Presurgical planning, including for instance virtual positioning of a dental implant may be provided based on the CT data or X-ray data. A surgical template may be produced from the 3D scan data, representing for instance the entire intra oral anatomy, that is matched with the CT data or X-ray data of the limited area. Thus the surgical template provides reliably inserting the dental implant into the patient, in accordance with the virtual planning.

For presurgical planning X-ray data may be used for planning angle, depth etc. when positioning an implant. The 3D scanned data may be used for three dimensional planning of the implant's direction with reference to the surgical template. In summary the data is sufficient to produce a precision surgical template. In this manner an advantageous ratio of resolution to patient dosage is achievable. By choosing or using a first input data source for the craniofacial structure, which is sufficiently well providing data for recognizing the craniofacial structure for enabling a pre-surgical planning of a dental restoration, patient dosage is lowered considerably. As mentioned above, data for jaw bone structure, nerve channels, but also other relevant bone structures, for instance needed for zygoma implants, have to be provided sufficiently for enabling reliable pre-surgical planning. However, high resolution CT scans having increased dosage are no longer necessary. Certain embodiments even totally eliminate the need of CT data for pre-surgical planning and/or production. For instance a CT scan may be replaced by an intra oral X-ray providing sufficient data for presurgical planning at a considerably lower patient dosage.

In another embodiment, 3D data for the jaw bone structure is acquired based on measurements of the patient's intra oral anatomy as well as measurements of the intra oral soft tissue, such that the 3D data for the jaw bone structure is concluded from these measurements. More precisely, a plaster cast of the patient's intra oral anatomy is made from the dental impression. A vacuum-pressed template is pressed over the plaster cast of the upper or lower jaw in order to produce a mapping guide. A series of holes is made in the mapping guide, for instance three buccal holes, three lingual/palatial holes and one hole on top of the crest at a site where a dental restoration is to be planned. Then the mapping guide placed in the patient's mouth and a probe is used to perforate the soft tissue through the holes in the mapping guide. Thereafter the mapping guide is removed from the patient's mouth. The thickness of the soft tissue is measured, for instance by inserting a probe with a scale and an endodontic disc, into the perforations in the soft tissue. Furthermore, the distance at a site of a missing tooth or several missing teeth between existing teeth is measured, giving a measure of the jaw bone in a longitudinal direction along the dental arch. The width of the jaw bone at the points where the thickness of the soft tissue is measured is determined by measuring the total width of the intra oral anatomy at the location of these points. This may be done by intra oral measurements or measuring the inner cross section of the mapping guide at the location of these points. By subtracting the thickness of the soft tissue from the total cross sectional measure, the thickness of the jaw bone at the puncture site is determined. The 3D data representing the topography of the jaw bone is determined by the plurality of measuring points. The 3D data may be entered into a CAD system for providing a virtual model of the jaw bone that may be matched with 3D data of the intra oral anatomy, e.g. by matching the position of the holes in the mapping guide with corresponding positions in the 3D data. This type of measurement data may be supplied in addition to match 2D X-ray data and 3D data. Planning is facilitated as information concerning 3D jaw bone topography may be used for improved planning.

Alternatively, 3D surface scanning of a mapping guide may be made in order to determine the topography of the mapping guide and holes therein. Thus 3D data of the mapping guide is available for matching with 3D data from a dental impression.

In still another embodiment, 3D data for the intra oral anatomy is acquired based on scanning a cast in plaster of the patient's intra oral anatomy. The cast is prepared from impressions taken from the patient, which then are filled with plaster. In this manner a positive plaster model of the intra oral anatomy is provided. The plaster model is scanned with a 3-D scanner, such as an optical 3D scanner or for instance the Procera Forte® surface probe scanner. 3D scanning of the plaster model provides high resolution 3D data of the patient's intra oral anatomy. 3D scanning may be done for a cast from each jaw separately. The 3D data of the patient model thus provided may for instance be used for production of dental restorations with high precision. The 3D data may be used in a medical workstation for planning a dental restorative procedure, when matched with data of the craniofacial anatomy, e.g. the topography of jaw bones, nerve channels therein etc.

Data for at least a part of the craniofacial anatomy may be obtained from CT scanning the craniofacial anatomy of the patient. In this manner CT data is obtained, as described above. The CT data may be matched with the 3D data obtained from 3D scanning the plaster model.

Suitable matching techniques comprise surface matching or contour matching. Surfaces may be identified in both CT data and 3D data. For instance in case the patient has teeth left and is not edentulous, a number of surfaces of teeth may be identified by suitable algorithms. CT data may be converted to a surface model of the intra oral anatomy. Corresponding surfaces may be identified in the 3D data and the CT data for matching of the data sets. Alternatively, or in combination, Contours may be identified in both the CT data and 3D data. CT data and 3D data may then matched by using the identified contours in both data sets.

Alternatively to the aforementioned CT data, data may be provided from other X-ray imaging sources, such as conventional 2D X-ray. For instance an intra oral X-ray is made, similar to the above described embodiment with reference to FIG. 20. Matching of the 2D X-ray data and the 3D data obtained from 3D scanning the plaster model may be made by means of contour matching. For instance a two dimensional (2D) contour is generated from the X-ray data, following for instance the contour of a tooth. A 2D section of the 3D data from the plaster model is made. The 2D contour is then searched in the 2D section of the plaster model 3D data. Matching is made by identifying the 2D contour both in the X-ray data set and the section of the 3D data set.

Alternatively, matching may be based on fiducial markers. Fiducial markers may for instance be attached appropriately to anatomical structures in the intra oral anatomy of the patient. For instance, fiducial markers may be attached to possibly existing teeth of the patient, e.g. by using a suitable adhesive substance. When taking an impression of the intra oral anatomy, the fiducial markers also shape the impression accordingly. When making a cast from the impression in order to provide the plaster model, the shape of the fiducial markers is transferred to the plaster model. In this manner 3D scanning the plaster model provides data for identifying the fiducial markers in the intra oral anatomy of the patient. The fiducial markers have a suitable shape for identification, e.g. semi spherical beads. Position of the fiducial markers in the 3D data set of the intra oral anatomy is obtained by finding the shape of these fiducial markers. Fiducial markers may for instance also be provided in form of a brace attached to the patient's teeth, or fiducial markers attached suitably to an existing brace. Thus position data for the fiducial markers is provided that may be matched with craniofacial data.

Craniofacial data may for instance be obtained by CT scanning with the fiducial markers in the same position as when taking the dental impression. Radio opaque fiducial markers are identified in the CT data set, providing the position thereof. Matching of the 3D data set with the CT data set is made by means of the identified positions of the fiducial markers.

In another embodiment, the intra oral anatomy 3D data obtained from the plaster model may be matched with 3D data for the jaw bone structure that is acquired based on measurements of the patient's intra oral anatomy as well as measurements of the intra oral soft tissue. In this case 3D data for the jaw bone structure is concluded from these measurements, as explained in more detail above. A plaster model of the patient's intra oral anatomy is made from a dental impression. The plaster model is both used for 3D scanning of the patient's intra oral anatomy, as well as for producing a mapping guide. A vacuum-pressed template is pressed over the plaster cast of the upper or lower jaw in order to produce the mapping guide. The mapping guide placed in the patient's mouth and a probe is used to perforate the soft tissue through the holes in the mapping guide and measurement data is provided for 3D data of the jaw bone structure and soft tissue. However, this 3D data from mapping by means of the probe does not have high resolution. Therefore, the plaster model may be used in the following manner. The topography corresponding to the soft tissue at the site of a dental restoration is at least partially removed from the plaster model, e.g. by grinding. In this manner a plaster model of the jaw bone structure is laid bare. The jaw bone plaster structure is then 3D scanned in order to provide a first data subset for the jaw bone structure. This first data subset for the jaw bone structure may provide a base for matching with other data sub sets of the intra oral anatomy or craniofacial anatomy. Then, the topography of the soft tissue is reconstructed on the jaw bone plaster model by means of gum replica material. Data for production of the topography of the soft tissue may be obtained from mapping by means of the probe. The plaster model with reconstructed soft tissue is then 3D scanned, providing a second data subset for the intra oral anatomy with soft tissue. 3D scanning is made in the same position of the plaster model as for generating the first data subset. The two data subsets may be matched, providing a combined data set for the 3D intra oral anatomy and jaw bone structure. Furthermore, a dental restoration may be attached to or in the plaster model having the replica gum attached thereto. The model with the jaw bone structure, the soft tissue and the dental restoration may be 3D scanned in order to obtain a third data subset for this configuration. 3D scanning is again made in the same position of the plaster model. Thus, the first, second and third data subset may be matched into a matched 3D data set. The matched 3D data set may be used independently for planning of surgical procedures and for providing data for producing dental restorations and/or product related to the surgical procedure. The matched 3D data set may be further matched with data obtained by CT scanning, X-ray etc. in order to increase flexibility.

As it is a requirement that the dental restoration does fit well into the existing oral structure of the patient, a second data input source that has a high resolution, e.g. a high resolution 3D scanning device, is used for providing input data for the existing oral structure. High resolution 3D data for the oral structure is provided from 3D scanning a dental impression.

By matching the data from the first input data source and the second data source, the high resolution is provided in the region where high precision is needed for the production of the dental restoration or product related to pre-surgical planning, i.e. in the region of the dentition. The high precision 3D data provides for a precise and reliable production of surgical templates, dental restorations, and products related thereto. Still, the input data from the first input data source provides sufficient information in order to provide for a reliable surgical planning.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

As will be appreciated by one of skill in the art, embodiments described herein may include a device, system, method or computer program product. Accordingly, embodiments may take the form of an entirely hardware embodiment, a software embodiment or an embodiment combining software and hardware aspects.

Furthermore, embodiments may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Embodiments are described herein with reference to flowchart and/or block diagrams. It will be understood that some or all of the illustrated blocks may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

It is to be understood that the functions/acts noted in the diagrams may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

The present disclosure has been described above with reference to specific embodiments. However, other embodiments than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

The invention claimed is:

1. A method for planning a dental restorative procedure, the planning comprising pre-surgical virtual positioning of a dental implant in a jawbone of a partially edentulous patient, and for producing at least one of a dental restoration and a product related to the dental restorative procedure, said method comprising matching first data of the patient's craniofacial area from a first data input source with second data of the patient's intra oral anatomy from a second data input source, different from said first data input source, into matched data for said planning and producing, the first data relating to tissue of the jawbone of the patient at a site for the dental restorative procedure and comprising data on a tooth of the patient, the second data relating to the site for the dental restorative procedure and comprising data on the tooth of the patient, wherein at least a part of said first data in said matched data is provided for said virtual positioning of the dental implant and at least a part of said second data in said matched data is provided for said producing; wherein said first data is obtained from an intra-oral 2D X-ray imaging device, wherein an X-ray sensitive apparatus is inserted into the patient's mouth; wherein said second data is obtained from a 3D scanner; wherein said first data obtained from the intra-oral 2D X-ray imaging device has a first resolution sufficient for enabling said planning; wherein said second data obtained from the 3D scanner has a second resolution sufficient for enabling said producing; wherein said first resolution is lower than said second resolution; wherein said matching comprises contour matching of contours identified in both said first data and said second data; and wherein said contour matching comprises:
   making a 2D section of the second data obtained from the 3D scanner;
   generating a 2D contour of the tooth from the first data obtained from the intra-oral 2D X-ray imaging device or from the 2D section; and
   identifying the 2D contour of the tooth in the first data when the 2D contour is generated from the 2D section and in the 2D section when the 2D contour is generated from the first data.

2. The method according to claim 1, wherein said second data is produced based on data obtained from said 3D scanner scanning a dental impression taken of the patient's intra oral anatomy.

3. The method according to claim 1, further comprising producing a surgical template based on said second data for installing the dental implant during said dental restorative procedure, wherein at least a part of said second data in said matched data is provided for said producing.

4. The method according to claim 1, further comprising controlling of production of a surgical template for said dental restorative procedure, wherein at least a part of said second data in said matched data is provided for said controlling.

5. The method according to claim 1, further comprising producing at least one of a dental restoration and a product related to the dental restorative procedure, wherein at least a part of said second data in said matched data is provided for said producing.

6. The method according to claim 5, wherein said producing comprises production of at least one dental implant, abutment, coping, bridge, inlay, onlay, anatomic abutment, anatomic crown, or crown.

7. The method according to claim 1, wherein the X-ray sensitive apparatus is a film plate.

8. The method according to claim 1, wherein the X-ray sensitive apparatus is a digital X-ray receiver.

9. The method according to claim 1, wherein the site for the dental restorative procedure comprises a tooth gap.

10. The method according to claim 9, wherein the first data comprises data for a tooth adjacent to the tooth gap.

11. The method according to claim 9, wherein the second data comprises data for a tooth adjacent to the tooth gap.

12. A system for planning a dental restorative procedure, the planning comprising pre-surgical virtual positioning of a dental implant in a jawbone of a partially edentulous patient, and for producing at least one of a dental restoration and a product related to the dental restorative procedure, said system comprising a matching unit for matching first data of the patient's craniofacial area from a first data input source with second data of the patient's intra oral anatomy from a second data input source, different from said first data input source, into matched data for said planning and producing, the first data relating to tissue of the jawbone of the patient at a site for the dental restorative procedure and comprising data on a tooth of the patient, the second data relating to the site for the dental restorative procedure and comprising data on the tooth of the patient, wherein at least a part of said first data in said matched data is provided for said virtual positioning of the dental implant and at least a part of said second data in said matched data is provided for said producing and wherein said first data is obtained from an intra-oral 2D X-ray imaging device, wherein an X-ray sensitive apparatus is configured to be inserted into the patient's mouth; wherein said second data is obtained from a 3D scanner; wherein said first data obtained from the intra-oral 2D X-ray imaging device has a first resolution sufficient for enabling said planning; wherein said second data obtained from the 3D scanner has a second resolution sufficient for enabling said producing; wherein said first resolution is lower than said second resolution; wherein said matching unit is configured to use contour matching of contours identified in both said first data and said second data; and wherein said contour matching comprises:

making a 2D section of the second data obtained from the 3D scanner;

generating a 2D contour of the tooth from the first data obtained from the intra-oral 2D X-ray imaging device or from the 2D section; and identifying the 2D contour of the tooth in the first data when the 2D contour is generated from the 2D section and in the 2D section when the 2D contour is generated from the first data.

13. The system according to claim 12, wherein the X-ray sensitive apparatus is a film plate.

14. The system according to claim 12, wherein the X-ray sensitive apparatus is a digital X-ray receiver.

15. A computer system programmed to perform a method for planning a dental restorative procedure, the planning comprising pre-surgical virtual positioning of a dental implant in a jawbone of a partially edentulous patient, and for producing at least one of a dental restoration and a product related to the dental restorative procedure, said method comprising matching first data of the patient's craniofacial area from a first data input source with second data of the patient's intra oral anatomy from a second data input source, different from said first data input source, into matched data for said planning and producing, the first data relating to tissue of the jawbone of the patient at a site for the dental restorative procedure and comprising data on a tooth of the patient, the second data relating to the site for the dental restorative procedure and comprising data on the tooth of the patient, wherein at least a part of said first data in said matched data is provided for said virtual positioning of the dental implant and at least a part of said second data in said matched data is provided for said producing; wherein said first data is obtained from an intra-oral 2D X-ray imaging device, wherein an X-ray sensitive apparatus is configured to be inserted into the patient's mouth; wherein said second data is obtained from a 3D scanner; wherein said first data obtained from the intra-oral 2D X-ray imaging device has a first resolution sufficient for enabling said planning; wherein said second data obtained from the 3D scanner has a second resolution sufficient for enabling said producing; wherein said first resolution is lower than said second resolution; wherein said matching comprises contour matching of contours identified in both said first data and said second data; and wherein said contour matching comprises:

making a 2D section of the second data obtained from the 3D scanner;

generating a 2D contour of the tooth from the first data obtained from the intra-oral 2D X-ray imaging device or from the 2D section; and identifying the 2D contour of the tooth in the first data when the 2D contour is generated from the 2D section and in the 2D section when the 2D contour is generated from the first data.

16. The system according to claim 15, wherein the X-ray sensitive apparatus is a film plate.

17. The system according to claim 15, wherein the X-ray sensitive apparatus is a digital X-ray receiver.

* * * * *